(12) United States Patent
Tucker et al.

(10) Patent No.: US 12,364,826 B2
(45) Date of Patent: Jul. 22, 2025

(54) ELECTRONIC CIGARETTE

(71) Applicant: Altria Client Services LLC, Richmond, VA (US)

(72) Inventors: Christopher S. Tucker, Midlothian, VA (US); Geoffrey Brandon Jordan, Midlothian, VA (US); Barry S. Smith, Hopewell, VA (US); Ali A. Rostami, Richmond, VA (US); Charles E. B. Glenn, Sr., Richmond, VA (US)

(73) Assignee: Altria Client Services LLC, Richmond, VA (US)

( * ) Notice: Subject to any disclaimer, the term of this patent is extended or adjusted under 35 U.S.C. 154(b) by 81 days.

(21) Appl. No.: 18/356,437

(22) Filed: Jul. 21, 2023

(65) Prior Publication Data

US 2023/0364364 A1 Nov. 16, 2023

Related U.S. Application Data

(60) Continuation of application No. 17/215,254, filed on Mar. 29, 2021, now Pat. No. 11,730,901, which is a
(Continued)

(51) Int. Cl.
*A24F 47/00* (2020.01)
*A24F 40/485* (2020.01)
(Continued)

(52) U.S. Cl.
CPC ........... *A61M 15/06* (2013.01); *A24F 40/485* (2020.01); *A24F 40/70* (2020.01); *A61M 11/003* (2014.02);
(Continued)

(58) Field of Classification Search
CPC ........... A24F 40/42; A24F 40/44; A24F 40/46
See application file for complete search history.

(56) References Cited

U.S. PATENT DOCUMENTS

| 539,839 A | 5/1895 | Voron |
| 751,923 A | 2/1904 | Kelly |

(Continued)

FOREIGN PATENT DOCUMENTS

| AU | 2013214987 B2 | 2/2017 |
| BE | 421623 A | 6/1937 |

(Continued)

OTHER PUBLICATIONS

Office Action dated Aug. 24, 2023 issued in related U.S. Appl. No. 16/784,357.
(Continued)

*Primary Examiner* — Eric Yaary
(74) *Attorney, Agent, or Firm* — Harness, Dickey & Pierce, P.L.C.

(57) ABSTRACT

An electronic cigarette includes a liquid supply including liquid material, a heater operable to heat the liquid material to a temperature sufficient to vaporize the liquid material and form an aerosol, a wick in communication with the liquid material and in communication with the heater such that the wick delivers the liquid material to the heater, at least one air inlet operable to deliver air to a central air passage upstream of the heater, and a mouth end insert having at least two diverging outlets. The electronic cigarette can also include an air flow diverter which directs incoming air away from a heating zone of the heater.

18 Claims, 10 Drawing Sheets

Related U.S. Application Data division of application No. 16/106,049, filed on Aug. 21, 2018, now Pat. No. 10,980,953, which is a division of application No. 15/065,422, filed on Mar. 9, 2016, now Pat. No. 10,092,037, which is a division of application No. 13/756,127, filed on Jan. 31, 2013, now Pat. No. 9,510,623.

(60) Provisional application No. 61/593,004, filed on Jan. 31, 2012.

(51) Int. Cl.

| | |
|---|---|
| *A24F 40/70* | (2020.01) |
| *A61M 11/00* | (2006.01) |
| *A61M 11/04* | (2006.01) |
| *A61M 15/06* | (2006.01) |
| *H01C 17/00* | (2006.01) |
| *H05B 1/02* | (2006.01) |
| *H05B 3/00* | (2006.01) |
| *H05B 3/10* | (2006.01) |
| *H05B 3/12* | (2006.01) |
| *H05B 3/16* | (2006.01) |
| *H05B 3/42* | (2006.01) |
| *H05B 3/44* | (2006.01) |
| *A24F 40/10* | (2020.01) |
| *A24F 40/40* | (2020.01) |
| *A24F 40/44* | (2020.01) |
| *A61M 15/00* | (2006.01) |
| *A61M 16/00* | (2006.01) |
| *A61M 21/00* | (2006.01) |

(52) U.S. Cl.
CPC .......... *A61M 11/042* (2014.02); *H01C 17/00* (2013.01); *H05B 1/0244* (2013.01); *H05B 3/0014* (2013.01); *H05B 3/10* (2013.01); *H05B 3/12* (2013.01); *H05B 3/16* (2013.01); *H05B 3/42* (2013.01); *H05B 3/44* (2013.01); *A24F 40/10* (2020.01); *A24F 40/40* (2020.01); *A24F 40/44* (2020.01); *A61M 11/001* (2014.02); *A61M 11/04* (2013.01); *A61M 15/002* (2014.02); *A61M 2016/0018* (2013.01); *A61M 2021/0016* (2013.01); *A61M 2205/3653* (2013.01); *A61M 2205/8206* (2013.01); *A61M 2205/8268* (2013.01); *A61M 2209/02* (2013.01); *F04C 2270/0421* (2013.01); *H05B 2203/021* (2013.01); *Y10T 29/49083* (2015.01)

(56) References Cited

U.S. PATENT DOCUMENTS

| | | |
|---|---|---|
| 777,948 A | 12/1904 | Gable |
| 811,859 A | 2/1906 | Marsh |
| 962,617 A | 6/1910 | Bucceri |
| 1,013,157 A | 1/1912 | Hadaway, Jr. |
| 1,185,661 A | 6/1916 | Hawley |
| 1,514,682 A | 11/1924 | Wilson |
| 1,557,351 A | 10/1925 | Fischer |
| 1,771,366 A | 7/1930 | Wyss et al. |
| 1,817,546 A | 8/1931 | Abraham |
| 1,841,952 A | 1/1932 | Hughes |
| 1,865,679 A | 7/1932 | Colpe |
| 1,865,780 A | 7/1932 | Naimaster |
| 1,916,799 A | 7/1933 | Hughes |
| 1,968,509 A | 7/1934 | Tiffany |
| 2,057,353 A | 10/1936 | Whittlemore, Jr. |
| 2,104,266 A | 1/1938 | McCormick |
| 2,356,975 A | 8/1944 | Comptois |
| 2,406,275 A | 8/1946 | Wejnarth |
| 2,442,004 A | 5/1948 | Hayward-Butt |
| 2,542,612 A | 2/1951 | Arneson |
| 2,558,127 A | 6/1951 | Downs |
| 2,599,310 A | 6/1952 | Abercrombie |
| 2,609,817 A | 9/1952 | Falcone |
| 2,670,739 A | 3/1954 | McNeill |
| 2,746,890 A | 5/1956 | Legler |
| 2,836,183 A | 5/1958 | Fay et al. |
| 2,907,686 A | 10/1959 | Siegel |
| 2,971,039 A | 2/1961 | Western |
| 2,972,557 A | 2/1961 | Toulmin, Jr. |
| 2,974,669 A | 3/1961 | Ellis |
| 3,062,218 A | 11/1962 | Temkovits |
| 3,150,668 A | 9/1964 | Lassiter et al. |
| 3,160,946 A | 12/1964 | Dickson, Jr. et al. |
| 3,200,819 A | 8/1965 | Gilbert |
| 3,255,760 A | 6/1966 | Selker |
| 3,258,015 A | 6/1966 | Ellis et al. |
| 3,294,095 A | 12/1966 | Ackerman |
| 3,347,231 A | 10/1967 | Chang |
| 3,356,094 A | 12/1967 | Ellis et al. |
| 3,363,633 A | 1/1968 | Weber |
| 3,396,733 A | 8/1968 | Allseits et al. |
| 3,402,723 A | 9/1968 | Hu |
| 3,425,414 A | 2/1969 | La Roche |
| 3,428,050 A | 2/1969 | Kandel |
| 3,439,685 A | 4/1969 | Allen |
| 3,482,580 A | 12/1969 | Hollabaugh |
| 3,521,643 A | 7/1970 | Toth |
| 3,559,300 A | 2/1971 | Fox |
| 3,581,748 A | 6/1971 | Cameron |
| 3,587,573 A | 6/1971 | Flack |
| 3,608,560 A | 9/1971 | Briskin et al. |
| 3,631,856 A | 1/1972 | Taylor |
| 3,681,018 A | 8/1972 | Karl-Georg et al. |
| 3,685,527 A | 8/1972 | Sherrill |
| 3,721,240 A | 3/1973 | Tamburri |
| 3,738,374 A | 6/1973 | Bennett |
| 3,744,496 A | 7/1973 | McCarty et al. |
| D229,789 S | 1/1974 | Berger |
| 3,789,840 A | 2/1974 | Rosenblatt |
| 3,804,100 A | 4/1974 | Fariello |
| 3,828,799 A | 8/1974 | Beam |
| 3,875,476 A | 4/1975 | Crandall et al. |
| 3,878,041 A | 4/1975 | Leitnaker et al. |
| 3,886,954 A | 6/1975 | Hannema et al. |
| 3,889,690 A | 6/1975 | Guarnieri |
| 3,895,219 A | 7/1975 | Richerson et al. |
| 3,943,941 A | 3/1976 | Boyd et al. |
| 4,016,061 A | 4/1977 | Wasa et al. |
| 4,068,672 A | 1/1978 | Guerra |
| 4,077,784 A | 3/1978 | Vayrynen |
| 4,083,372 A | 4/1978 | Boden |
| 4,098,725 A | 7/1978 | Yamamoto et al. |
| 4,110,260 A | 8/1978 | Yamamoto et al. |
| 4,131,119 A | 12/1978 | Blasutti |
| 4,141,369 A | 2/1979 | Burruss |
| 4,149,548 A | 4/1979 | Bradshaw |
| 4,164,230 A | 8/1979 | Pearlman |
| 4,193,411 A | 3/1980 | Faris et al. |
| 4,215,708 A | 8/1980 | Bron |
| 4,219,032 A | 8/1980 | Tabatznik et al. |
| 4,246,913 A | 1/1981 | Ogden et al. |
| 4,256,945 A | 3/1981 | Carter et al. |
| 4,259,970 A | 4/1981 | Green, Jr. |
| 4,275,747 A | 6/1981 | Miller |
| 4,284,089 A | 8/1981 | Ray |
| 4,331,166 A | 5/1982 | Hale |
| 4,413,641 A | 11/1983 | Dwyer, Jr. et al. |
| 4,419,302 A | 12/1983 | Nishino et al. |
| 4,429,703 A | 2/1984 | Haber |
| 4,430,072 A | 2/1984 | Kellogg et al. |
| 4,446,878 A | 5/1984 | Porenski, Jr. |
| 4,457,319 A | 7/1984 | Lamb et al. |
| 4,476,882 A | 10/1984 | Luke |
| 4,493,331 A | 1/1985 | Porenski, Jr. |
| 4,506,683 A | 3/1985 | Cantrell et al. |
| 4,515,170 A | 5/1985 | Cantrell et al. |
| 4,517,996 A | 5/1985 | Vester |
| 4,582,072 A | 4/1986 | Sanford |

(56) References Cited

U.S. PATENT DOCUMENTS

| | | |
|---|---|---|
| 4,620,557 A | 11/1986 | Cantrell et al. |
| 4,649,944 A | 3/1987 | Houck, Jr. et al. |
| 4,649,945 A | 3/1987 | Norman et al. |
| 4,681,125 A | 7/1987 | Johnson |
| 4,687,008 A | 8/1987 | Houck, Jr. et al. |
| 4,735,217 A | 4/1988 | Gerth et al. |
| 4,765,347 A | 8/1988 | Sensabaugh, Jr. et al. |
| 4,776,353 A | 10/1988 | Lilja et al. |
| 4,804,002 A | 2/1989 | Herron |
| 4,848,376 A | 7/1989 | Lilja et al. |
| 4,922,901 A | 5/1990 | Brooks et al. |
| 4,941,486 A | 7/1990 | Dube et al. |
| 4,945,929 A | 8/1990 | Egilmex |
| 4,945,931 A | 8/1990 | Gori |
| 4,947,874 A | 8/1990 | Brooks et al. |
| 4,947,875 A | 8/1990 | Brooks et al. |
| 4,966,171 A | 10/1990 | Serrano et al. |
| 4,981,522 A | 1/1991 | Nichols et al. |
| 4,991,606 A | 2/1991 | Serrano et al. |
| 4,993,436 A | 2/1991 | Bloom, Jr. |
| 5,000,228 A | 3/1991 | Manent et al. |
| 5,016,656 A | 5/1991 | McMurtrie |
| 5,040,552 A | 8/1991 | Schleich et al. |
| 5,042,510 A | 8/1991 | Curtiss et al. |
| 5,045,237 A | 9/1991 | Washburn |
| 5,060,671 A | 10/1991 | Counts et al. |
| 5,076,296 A | 12/1991 | Nystrom et al. |
| 5,085,804 A | 2/1992 | Washburn |
| 5,093,894 A | 3/1992 | Deevi et al. |
| 5,095,921 A | 3/1992 | Losee et al. |
| 5,116,298 A | 5/1992 | Bondanelli et al. |
| 5,137,578 A | 8/1992 | Chan |
| 5,139,594 A | 8/1992 | Rabin |
| 5,144,962 A | 9/1992 | Counts et al. |
| 5,144,964 A | 9/1992 | Demain |
| 5,157,242 A | 10/1992 | Hetherington et al. |
| 5,159,940 A | 11/1992 | Hayward et al. |
| 5,179,966 A | 1/1993 | Losee et al. |
| 5,224,498 A | 7/1993 | Deevi et al. |
| 5,228,460 A | 7/1993 | Sprinkel et al. |
| 5,235,157 A | 8/1993 | Blackburn |
| 5,249,586 A | 10/1993 | Morgan et al. |
| 5,269,327 A | 12/1993 | Counts et al. |
| 5,274,214 A | 12/1993 | Blackburn |
| 5,285,050 A | 2/1994 | Blackburn |
| 5,322,075 A | 6/1994 | Deevi et al. |
| 5,353,813 A | 10/1994 | Deevi et al. |
| 5,369,723 A | 11/1994 | Counts et al. |
| 5,388,594 A | 2/1995 | Counts et al. |
| 5,396,911 A | 3/1995 | Casey, III et al. |
| 5,408,574 A | 4/1995 | Deevi et al. |
| 5,473,251 A | 12/1995 | Mori |
| 5,498,855 A | 3/1996 | Deevi et al. |
| 5,505,214 A | 4/1996 | Collins et al. |
| 5,514,630 A | 5/1996 | Willkens et al. |
| 5,591,368 A | 1/1997 | Fleischhauer et al. |
| 5,595,706 A | 1/1997 | Sikka et al. |
| 5,611,360 A | 3/1997 | Tang |
| 5,613,504 A | 3/1997 | Collins et al. |
| 5,613,505 A | 3/1997 | Campbell et al. |
| 5,665,262 A | 9/1997 | Hajaligol et al. |
| 5,666,977 A | 9/1997 | Higgins et al. |
| 5,666,978 A | 9/1997 | Counts et al. |
| 5,692,291 A | 12/1997 | Deevi et al. |
| 5,724,997 A | 3/1998 | Smith et al. |
| 5,730,158 A | 3/1998 | Collins et al. |
| 5,743,251 A | 4/1998 | Howell et al. |
| 5,865,185 A | 2/1999 | Collins et al. |
| 5,865,186 A | 2/1999 | Volsey, II |
| 5,878,752 A | 3/1999 | Adams et al. |
| 5,894,841 A | 4/1999 | Voges |
| 5,924,417 A | 7/1999 | Braithwaite |
| 5,935,975 A | 8/1999 | Rose et al. |
| 6,006,757 A | 12/1999 | Lichtenberg |
| 6,016,801 A | 1/2000 | Philips |
| 6,026,820 A | 2/2000 | Baggett, Jr. et al. |
| 6,155,268 A | 12/2000 | Takeuchi |
| 6,164,287 A | 12/2000 | White |
| 6,196,218 B1 | 3/2001 | Voges |
| 6,234,167 B1 | 5/2001 | Cox et al. |
| 6,371,127 B1 | 4/2002 | Snaidr et al. |
| 6,443,146 B1 | 9/2002 | Voges |
| 6,516,796 B1 | 2/2003 | Cox et al. |
| 6,598,607 B2 | 7/2003 | Adiga et al. |
| 6,615,840 B1 | 9/2003 | Fournier et al. |
| 6,715,487 B2 | 4/2004 | Nichols et al. |
| 6,772,756 B2 | 8/2004 | Shayan |
| 6,806,682 B2 | 10/2004 | Hsiao |
| 6,810,883 B2 | 11/2004 | Felter et al. |
| 6,854,470 B1 | 2/2005 | Pu |
| 6,994,096 B2 | 2/2006 | Rostami et al. |
| 7,073,499 B1 | 7/2006 | Reinhold et al. |
| 7,117,867 B2 | 10/2006 | Cox et al. |
| 7,131,599 B2 | 11/2006 | Katase |
| 7,167,641 B2 | 1/2007 | Tam et al. |
| 7,381,277 B2 | 6/2008 | Gonterman et al. |
| 7,404,405 B1 | 7/2008 | Mehio |
| 7,458,374 B2 | 12/2008 | Hale et al. |
| D590,988 S | 4/2009 | Hon |
| D590,989 S | 4/2009 | Hon |
| D590,990 S | 4/2009 | Hon |
| D590,991 S | 4/2009 | Hon |
| 7,527,059 B2 | 5/2009 | Iannuzzi |
| 7,614,402 B2 | 11/2009 | Gomes |
| 7,726,320 B2 | 6/2010 | Robinson et al. |
| 7,789,089 B2 | 9/2010 | Dube et al. |
| 7,810,508 B2 | 10/2010 | Wyss-Peters et al. |
| 7,832,410 B2 | 11/2010 | Hon |
| 7,845,359 B2 | 12/2010 | Montaser |
| 7,878,962 B2 | 2/2011 | Karles et al. |
| 7,906,936 B2 | 3/2011 | Azancot et al. |
| 7,913,688 B2 | 3/2011 | Cross et al. |
| 7,920,777 B2 | 4/2011 | Rabin et al. |
| 7,938,124 B2 | 5/2011 | Izumiya et al. |
| 7,952,322 B2 | 5/2011 | Partovi et al. |
| 7,997,280 B2 | 8/2011 | Rosenthal |
| D646,431 S | 10/2011 | Awty et al. |
| D651,338 S | 12/2011 | Awty et al. |
| 8,079,371 B2 | 12/2011 | Robinson et al. |
| D653,390 S | 1/2012 | Kaljura |
| D655,036 S | 2/2012 | Zhou |
| 8,113,215 B2 | 2/2012 | Rasouli et al. |
| 8,118,161 B2 | 2/2012 | Guerrera et al. |
| 8,127,772 B2 | 3/2012 | Montaser |
| 8,156,944 B2 | 4/2012 | Han |
| 8,157,918 B2 | 4/2012 | Becker et al. |
| 8,196,576 B2 | 6/2012 | Kriksunov et al. |
| 8,205,622 B2 | 6/2012 | Pan |
| 8,258,192 B2 | 9/2012 | Wu et al. |
| 8,314,591 B2 | 11/2012 | Terry et al. |
| 8,365,742 B2 | 2/2013 | Hon |
| 8,371,310 B2 | 2/2013 | Brenneise |
| 8,375,957 B2 | 2/2013 | Hon |
| 8,393,331 B2 | 3/2013 | Hon |
| D684,311 S | 6/2013 | Liu |
| 8,459,270 B2 | 6/2013 | Coven et al. |
| 8,459,271 B2 | 6/2013 | Inagaki |
| 8,499,766 B1 | 8/2013 | Newton |
| 8,511,318 B2 | 8/2013 | Hon |
| 8,550,068 B2 | 10/2013 | Terry et al. |
| 8,550,069 B2 | 10/2013 | Alelov |
| 8,689,805 B2 | 4/2014 | Hon |
| 8,833,364 B2 | 9/2014 | Buchberger |
| 8,915,254 B2 | 12/2014 | Monsees et al. |
| 8,960,197 B2 | 2/2015 | Bailey et al. |
| 9,078,473 B2 | 7/2015 | Worm et al. |
| 9,078,474 B2 | 7/2015 | Thompson |
| 9,204,670 B2 | 12/2015 | Liu |
| 9,282,772 B2 | 3/2016 | Tucker et al. |
| 9,326,547 B2 | 5/2016 | Tucker et al. |
| 9,351,522 B2 | 5/2016 | Safari |
| 9,408,416 B2 | 8/2016 | Monsees et al. |
| 9,474,306 B2 | 10/2016 | Tucker et al. |
| 9,510,623 B2 | 12/2016 | Tucker et al. |

(56) References Cited

U.S. PATENT DOCUMENTS

| | | |
|---|---|---|
| 9,854,839 B2 | 1/2018 | Tucker et al. |
| 2002/0005207 A1 | 1/2002 | Wrenn et al. |
| 2002/0179101 A1 | 12/2002 | Chavez |
| 2004/0020500 A1 | 2/2004 | Wrenn et al. |
| 2004/0050396 A1 | 3/2004 | Squeo |
| 2004/0099266 A1 | 5/2004 | Cross et al. |
| 2004/0149296 A1 | 8/2004 | Rostami et al. |
| 2005/0016550 A1 | 1/2005 | Katase |
| 2005/0016553 A1 | 1/2005 | Iannuzzi |
| 2005/0067503 A1 | 3/2005 | Katase |
| 2005/0126651 A1 | 6/2005 | Sherwin |
| 2005/0175331 A1 | 8/2005 | Tam et al. |
| 2005/0279371 A1 | 12/2005 | Billard et al. |
| 2006/0070633 A1 | 4/2006 | Rostami et al. |
| 2006/0191546 A1 | 8/2006 | Takano et al. |
| 2006/0196518 A1 | 9/2006 | Hon |
| 2006/0254604 A1 | 11/2006 | Martinez Fernandez |
| 2007/0074734 A1 | 4/2007 | Braunshteyn et al. |
| 2007/0095357 A1 | 5/2007 | Besso et al. |
| 2007/0098148 A1 | 5/2007 | Sherman |
| 2007/0102013 A1 | 5/2007 | Adams et al. |
| 2007/0267031 A1 | 11/2007 | Hon |
| 2007/0267032 A1 | 11/2007 | Shan |
| 2007/0279002 A1 | 12/2007 | Partovi |
| 2007/0280653 A1 | 12/2007 | Viera |
| 2007/0295332 A1 | 12/2007 | Ziegler et al. |
| 2008/0038363 A1 | 2/2008 | Zaffaroni et al. |
| 2008/0047571 A1 | 2/2008 | Braunshteyn et al. |
| 2008/0092912 A1 | 4/2008 | Robinson et al. |
| 2008/0230052 A1 | 9/2008 | Montaser |
| 2008/0276947 A1 | 11/2008 | Martzel |
| 2009/0007925 A1 | 1/2009 | Rasouli et al. |
| 2009/0012655 A1 | 1/2009 | Kienman et al. |
| 2009/0044816 A1 | 2/2009 | Rasouli et al. |
| 2009/0056729 A1 | 3/2009 | Zawadzki et al. |
| 2009/0065011 A1 | 3/2009 | Maeder et al. |
| 2009/0084391 A1 | 4/2009 | Krupp |
| 2009/0095311 A1 | 4/2009 | Han |
| 2009/0126745 A1 | 5/2009 | Hon |
| 2009/0133704 A1 | 5/2009 | Strickland et al. |
| 2009/0139517 A1 | 6/2009 | Wachtel et al. |
| 2009/0139533 A1 | 6/2009 | Park et al. |
| 2009/0151717 A1 | 6/2009 | Bowen et al. |
| 2009/0162294 A1 | 6/2009 | Werner |
| 2009/0188490 A1 | 7/2009 | Han |
| 2009/0230117 A1 | 9/2009 | Fernando et al. |
| 2009/0272379 A1 | 11/2009 | Thorens et al. |
| 2009/0283103 A1 | 11/2009 | Nielsen et al. |
| 2009/0293892 A1 | 12/2009 | Williams et al. |
| 2009/0301502 A1 | 12/2009 | Mehio |
| 2010/0031968 A1 | 2/2010 | Sheikh et al. |
| 2010/0083959 A1 | 4/2010 | Siller |
| 2010/0126505 A1 | 5/2010 | Rinker |
| 2010/0200006 A1 | 8/2010 | Robinson et al. |
| 2010/0200008 A1 | 8/2010 | Taieb |
| 2010/0206317 A1 | 8/2010 | Albino et al. |
| 2010/0242974 A1 | 9/2010 | Pan |
| 2010/0242975 A1 | 9/2010 | Hearn |
| 2010/0242976 A1 | 9/2010 | Katayama et al. |
| 2010/0275938 A1 | 11/2010 | Roth et al. |
| 2010/0307518 A1 | 12/2010 | Wang |
| 2011/0005535 A1 | 1/2011 | Xiu |
| 2011/0011394 A1 | 1/2011 | Edwards et al. |
| 2011/0011396 A1 | 1/2011 | Fang |
| 2011/0036346 A1 | 2/2011 | Cohen et al. |
| 2011/0036363 A1 | 2/2011 | Urtsev et al. |
| 2011/0036367 A1 | 2/2011 | Saito et al. |
| 2011/0088707 A1 | 4/2011 | Hajaligol |
| 2011/0094523 A1 | 4/2011 | Thorens et al. |
| 2011/0120455 A1 | 5/2011 | Murphy |
| 2011/0120482 A1 | 5/2011 | Brenneise |
| 2011/0126848 A1 | 6/2011 | Zuber et al. |
| 2011/0147486 A1 | 6/2011 | Greim et al. |
| 2011/0155153 A1 | 6/2011 | Thorens et al. |
| 2011/0168194 A1 | 7/2011 | Hon |
| 2011/0209717 A1 | 9/2011 | Han |
| 2011/0220134 A1 | 9/2011 | Duke et al. |
| 2011/0226236 A1 | 9/2011 | Buchberger |
| 2011/0232654 A1 | 9/2011 | Mass |
| 2011/0245493 A1 | 10/2011 | Rabinowitz et al. |
| 2011/0253798 A1 | 10/2011 | Tucker et al. |
| 2011/0265806 A1 | 11/2011 | Alarcon et al. |
| 2011/0277756 A1 | 11/2011 | Terry et al. |
| 2011/0277757 A1 | 11/2011 | Terry et al. |
| 2011/0277760 A1 | 11/2011 | Terry et al. |
| 2011/0277761 A1 | 11/2011 | Terry et al. |
| 2011/0277764 A1 | 11/2011 | Terry et al. |
| 2011/0277780 A1 | 11/2011 | Terry et al. |
| 2011/0278189 A1 | 11/2011 | Terry et al. |
| 2011/0290244 A1 | 12/2011 | Schennum |
| 2011/0290268 A1 | 12/2011 | Schennum |
| 2011/0303231 A1 | 12/2011 | Li et al. |
| 2011/0304282 A1 | 12/2011 | Li et al. |
| 2012/0006342 A1 | 1/2012 | Rose et al. |
| 2012/0048266 A1 | 3/2012 | Alelov |
| 2012/0090629 A1 | 4/2012 | Turner et al. |
| 2012/0111347 A1 | 5/2012 | Hon |
| 2012/0118301 A1 | 5/2012 | Montaser |
| 2012/0145169 A1 | 6/2012 | Wu |
| 2012/0167906 A1 | 7/2012 | Gysland |
| 2012/0174914 A1 | 7/2012 | Pirshafiey et al. |
| 2012/0186594 A1 | 7/2012 | Liu |
| 2012/0199146 A1 | 8/2012 | Marangos |
| 2012/0199663 A1 | 8/2012 | Qiu |
| 2012/0201522 A1 | 8/2012 | Stauffer et al. |
| 2012/0211015 A1 | 8/2012 | Li et al. |
| 2012/0227753 A1 | 9/2012 | Newton |
| 2012/0230659 A1 | 9/2012 | Goodman et al. |
| 2012/0260927 A1 | 10/2012 | Liu |
| 2012/0285475 A1 | 11/2012 | Liu |
| 2012/0285476 A1 | 11/2012 | Hon |
| 2012/0312313 A1 | 12/2012 | Frija |
| 2012/0318882 A1 | 12/2012 | Abehasera |
| 2012/0325227 A1 | 12/2012 | Robinson et al. |
| 2013/0014772 A1 | 1/2013 | Liu |
| 2013/0019887 A1 | 1/2013 | Liu |
| 2013/0025609 A1 | 1/2013 | Liu |
| 2013/0026798 A1 | 1/2013 | Meier |
| 2013/0032159 A1 | 2/2013 | Capuano |
| 2013/0032161 A1 | 2/2013 | Herholdt |
| 2013/0037041 A1 | 2/2013 | Worm et al. |
| 2013/0061861 A1 | 3/2013 | Hearn |
| 2013/0081642 A1 | 4/2013 | Safari |
| 2013/0087160 A1 | 4/2013 | Gherghe |
| 2013/0118509 A1 | 5/2013 | Richardson |
| 2013/0125906 A1 | 5/2013 | Hon |
| 2013/0139833 A1 | 6/2013 | Hon |
| 2013/0152922 A1 | 6/2013 | Benassayag et al. |
| 2013/0168880 A1 | 7/2013 | Duke |
| 2013/0192615 A1 | 8/2013 | Tucker et al. |
| 2013/0192616 A1 | 8/2013 | Tucker et al. |
| 2013/0192619 A1 | 8/2013 | Tucker et al. |
| 2013/0192620 A1 | 8/2013 | Tucker et al. |
| 2013/0192621 A1 | 8/2013 | Li et al. |
| 2013/0192622 A1 | 8/2013 | Tucker et al. |
| 2013/0192623 A1 | 8/2013 | Tucker et al. |
| 2013/0206154 A1 | 8/2013 | Fernando et al. |
| 2013/0213418 A1 | 8/2013 | Tucker et al. |
| 2013/0213419 A1 | 8/2013 | Tucker et al. |
| 2013/0213420 A1 | 8/2013 | Hon |
| 2013/0220315 A1 | 8/2013 | Conley et al. |
| 2013/0228191 A1 | 9/2013 | Newton |
| 2013/0263869 A1 | 10/2013 | Zhu |
| 2013/0276798 A1 | 10/2013 | Hon |
| 2013/0298905 A1 | 11/2013 | Levin et al. |
| 2013/0300350 A1 | 11/2013 | Xiang |
| 2013/0319440 A1 | 12/2013 | Capuano |
| 2014/0000638 A1 | 1/2014 | Sebastian et al. |
| 2014/0007863 A1 | 1/2014 | Chen |
| 2014/0034071 A1 | 2/2014 | Levitz et al. |
| 2014/0196718 A1 | 7/2014 | Li et al. |
| 2014/0209110 A1 | 7/2014 | Hon |
| 2014/0262869 A1 | 9/2014 | Fath et al. |
| 2014/0262871 A1 | 9/2014 | Fath |

(56) References Cited

U.S. PATENT DOCUMENTS

| | | | |
|---|---|---|---|
| 2014/0262931 A1 | 9/2014 | Fath | |
| 2014/0338680 A1 | 11/2014 | Abramov et al. | |
| 2015/0020831 A1 | 1/2015 | Weigensberg et al. | |
| 2015/0128974 A1 | 5/2015 | Hon | |
| 2015/0250232 A1 | 9/2015 | Hon | |

FOREIGN PATENT DOCUMENTS

| | | | |
|---|---|---|---|
| CA | 1202378 A | 3/1986 | |
| CH | 421786 A | 9/1966 | |
| CH | 698603 B1 | 9/2009 | |
| CN | 87/104459 A | 2/1988 | |
| CN | 2243191 Y | 12/1996 | |
| CN | 1191696 A | 9/1998 | |
| CN | 1196660 A | 10/1998 | |
| CN | 2293953 Y | 10/1998 | |
| CN | 1229616 A | 9/1999 | |
| CN | 2719043 Y | 8/2005 | |
| CN | 277799 | 5/2006 | |
| CN | 2777995 Y | 5/2006 | |
| CN | 1906096 A | 1/2007 | |
| CN | 2889333 Y | 4/2007 | |
| CN | 101116542 A | 2/2008 | |
| CN | 201018927 Y | 2/2008 | |
| CN | 201029436 Y | 3/2008 | |
| CN | 100377672 C | 4/2008 | |
| CN | 201054977 Y | 5/2008 | |
| CN | 201067079 Y | 6/2008 | |
| CN | 201076006 Y | 6/2008 | |
| CN | 201079011 Y | 7/2008 | |
| CN | 201085044 Y | 7/2008 | |
| CN | 201108031 Y | 9/2008 | |
| CN | 201127293 Y | 10/2008 | |
| CN | 201146824 Y | 11/2008 | |
| CN | 10132257 | 12/2008 | |
| CN | 101322579 A | 12/2008 | |
| CN | 201238610 Y | 5/2009 | |
| CN | 101518361 A | 9/2009 | |
| CN | 101524187 A | 9/2009 | |
| CN | 101557728 A | 10/2009 | |
| CN | 201379072 Y | 1/2010 | |
| CN | 101843368 A | 9/2010 | |
| CN | 20170939 | 1/2011 | |
| CN | 201709398 U | 1/2011 | |
| CN | 101983018 A | 3/2011 | |
| CN | 201767027 U | 3/2011 | |
| CN | 20178992 | 4/2011 | |
| CN | 20179799 | 4/2011 | |
| CN | 101606758 B | 4/2011 | |
| CN | 102014996 A | 4/2011 | |
| CN | 201789924 U | 4/2011 | |
| CN | 201797997 U | 4/2011 | |
| CN | 201830900 U | 5/2011 | |
| CN | 10210661 | 6/2011 | |
| CN | 102106611 A | 6/2011 | |
| CN | 201860753 U | 6/2011 | |
| CN | 201869778 U | 6/2011 | |
| CN | 10216604 | 8/2011 | |
| CN | 102166044 A | 8/2011 | |
| CN | 201986689 U | 9/2011 | |
| CN | 202014571 | 10/2011 | |
| CN | 202014571 U | 10/2011 | |
| CN | 202014572 U | 10/2011 | |
| CN | 202026802 | 10/2011 | |
| CN | 102264420 A | 11/2011 | |
| CN | 102264423 A | 11/2011 | |
| CN | 202026804 U | 11/2011 | |
| CN | 102266125 A | 12/2011 | |
| CN | 202068930 U | 12/2011 | |
| CN | 202068932 U | 12/2011 | |
| CN | 202122097 U | 1/2012 | |
| CN | 202145881 U | 2/2012 | |
| CN | 202179125 U | 4/2012 | |
| CN | 202233005 U | 5/2012 | |
| CN | 202233007 U | 5/2012 | |
| CN | 202262413 U | 6/2012 | |
| CN | 202286307 U | 7/2012 | |
| CN | 102655773 A | 9/2012 | |
| CN | 202445135 U | 9/2012 | |
| CN | 102740716 A | 10/2012 | |
| CN | 202456410 U | 10/2012 | |
| CN | 202525085 U | 11/2012 | |
| CN | 202603603 U | 12/2012 | |
| CN | 202603608 U | 12/2012 | |
| CN | 102894485 A | 1/2013 | |
| DE | 3640917 A1 | 8/1988 | |
| DE | 3735704 A1 | 5/1989 | |
| DE | 19854009 A1 | 5/2000 | |
| DE | 19935706 A1 | 2/2001 | |
| DE | 69824982 T2 | 10/2004 | |
| DE | 202010011436 U1 | 11/2010 | |
| EP | 0893071 A1 | 7/1908 | |
| EP | 0117355 A2 | 9/1984 | |
| EP | 0277519 A2 | 8/1988 | |
| EP | 0295122 A2 | 12/1988 | |
| EP | 0358002 A2 | 3/1990 | |
| EP | 0358114 A2 | 3/1990 | |
| EP | 0430566 A2 | 6/1991 | |
| EP | 438862 A2 | 7/1991 | |
| EP | 0488488 A1 | 6/1992 | |
| EP | 0503767 A1 | 9/1992 | |
| EP | 0608783 A1 | 8/1994 | |
| EP | 0845220 A1 | 6/1998 | |
| EP | 0857431 A1 | 8/1998 | |
| EP | 1618803 A1 | 1/2006 | |
| EP | 1736065 A1 | 12/2006 | |
| EP | 1989946 A1 | 11/2008 | |
| EP | 2022350 A1 | 2/2009 | |
| EP | 2110033 A1 | 10/2009 | |
| EP | 2113178 A1 | 11/2009 | |
| EP | 2260733 A1 | 12/2010 | |
| EP | 2481308 A1 | 8/2012 | |
| EP | 2809180 B1 | 12/2019 | |
| ES | 1070376 Y | 11/2009 | |
| GB | 203964 | 9/1923 | |
| GB | 2148079 A | 5/1985 | |
| GB | 2406780 A | 4/2005 | |
| JP | 61068061 A | 4/1986 | |
| JP | H11164679 A | 6/1999 | |
| JP | 2003527127 A | 9/2003 | |
| JP | 2006/320286 A | 11/2006 | |
| JP | 2007511437 A | 5/2007 | |
| JP | 2009-537120 A | 10/2009 | |
| JP | 2010-104310 A | 5/2010 | |
| JP | 2010-213579 A | 9/2010 | |
| JP | 3164992 U | 12/2010 | |
| KR | 100636287 B1 | 10/2006 | |
| KR | 200454110 Y1 | 6/2011 | |
| KR | 2011-0006928 U | 7/2011 | |
| KR | 101081481 B1 | 11/2011 | |
| KR | 20110010862 U | 11/2011 | |
| KR | 200457340 Y1 | 12/2011 | |
| NL | 8201585 A | 11/1982 | |
| RU | 94815 U1 | 6/2010 | |
| WO | WO-86/02528 A1 | 5/1986 | |
| WO | WO-9003224 A1 | 4/1990 | |
| WO | WO-95/02970 A1 | 2/1995 | |
| WO | WO-97/048293 A1 | 12/1997 | |
| WO | WO-9843019 A1 | 10/1998 | |
| WO | WO-00/28843 A1 | 5/2000 | |
| WO | WO-0170054 A1 | 9/2001 | |
| WO | WO-03037412 A2 | 5/2003 | |
| WO | WO-03/080149 A2 | 10/2003 | |
| WO | WO-2004/043175 A1 | 5/2004 | |
| WO | WO-2004/054647 A1 | 7/2004 | |
| WO | WO-2004/080216 A1 | 9/2004 | |
| WO | WO-2004/095955 A1 | 11/2004 | |
| WO | WO-2005049449 A1 | 6/2005 | |
| WO | WO-2005/099494 A1 | 10/2005 | |
| WO | WO-2005120614 A1 | 12/2005 | |
| WO | WO-2007024130 A1 | 3/2007 | |
| WO | WO-2007/066374 A1 | 6/2007 | |
| WO | WO-2007/078273 A1 | 7/2007 | |
| WO | WO-2007/098337 A2 | 8/2007 | |

(56) References Cited

FOREIGN PATENT DOCUMENTS

| WO | WO-2007/131449 A1 | 11/2007 |
|---|---|---|
| WO | WO-2007/131450 A1 | 11/2007 |
| WO | WO-2007/141668 A2 | 12/2007 |
| WO | WO-2008/055423 A1 | 5/2008 |
| WO | WO-2009135729 A1 | 11/2009 |
| WO | WO-2010091593 A1 | 8/2010 |
| WO | WO-2010/145468 A1 | 12/2010 |
| WO | WO-2011015825 A1 | 2/2011 |
| WO | WO-2011/050943 A1 | 5/2011 |
| WO | WO-2011/121326 A2 | 10/2011 |
| WO | WO-2011/124033 A1 | 10/2011 |
| WO | WO-2011/125058 A1 | 10/2011 |
| WO | WO-2011/146372 A2 | 11/2011 |
| WO | WO-2011146174 A2 | 11/2011 |
| WO | WO-2011147714 A1 | 12/2011 |
| WO | WO-2012/088675 A1 | 7/2012 |
| WO | WO-2012/109371 A2 | 8/2012 |
| WO | WO-2012/129787 A1 | 10/2012 |
| WO | WO-2012/129812 A1 | 10/2012 |
| WO | WO-2012/142293 A2 | 10/2012 |
| WO | WO-2012/152053 A1 | 11/2012 |
| WO | WO-2013116565 A1 | 8/2013 |

OTHER PUBLICATIONS

Extended European Search Report dated Mar. 20, 2024 issued in European patent application No. 24159503.2.
Office Action dated May 28, 2024 issued in U.S. Appl. No. 16/784,357.
International Search Report and Written Opinion for PCT/US13/24228 dated Apr. 9, 2013.
International Search Report and Written Opinion for PCT/US13/24229 dated Apr. 22, 2013.
International Search Report and Written Opinion for PCT/US13/24215 dated Apr. 22, 2013.
International Search Report and Written Opinion for PCT/US13/24222 dated Apr. 24, 2013.
International Search Report and Written Opinion for PCT/US13/27424 dated Apr. 25, 2013.
International Search Report and Written Opinion for PCT/US13/24224 dated May 13, 2013.
U.S. Appl. No. 13/843,028, filed Mar. 15, 2013, to Fath et al.
U.S. Appl. No. 13/843,449, filed Mar. 15, 2013, to Fath et al.
International Search Report and Written Opinion for PCT/US13/24219 dated Apr. 22, 2013.
U.S. Appl. No. 13/843,314, filed Mar. 15, 2013, to Fath et al.
International Search Report and Written Opinion for PCT/US13/24211 dated Apr. 19, 2013.
DE 19935706 Translation; Feb. 2001, Kumar Zubide.
Moroccan Office Action dated Mar. 13, 2015 issued in corresponding Moroccan Application No. 37287.
European Search Report dated May 29, 2015 issued in corresponding European Patent Application No. 13744358.6.
European Search Report dated Jul. 9, 2015 issued in corresponding European Patent Application No. 13743475.9.
Office Action for corresponding Chinese application No. 201380007594.2 dated Nov. 23, 2015 and English Translation thereof.
Notice of Allowance for co-related U.S. Appl. No. 13/741,217 dated Nov. 9, 2015.
Office Action for corresponding Chinese application No. 201380018495.4 dated Jan. 4, 2016 and English Translation thereof.
Kazakhstan Office Action dated Mar. 11, 2016 for corresponding KZ Application No. 2014/1685.1.
USPTO non-final Office Action dated Apr. 5, 2016 in U.S. Appl. No. 13/756,127.
International Search Report and Written Opinion for PCT/US13/27432 dated May 2, 2013.
International Preliminary Report on Patentability for PCT/US2013/024215 dated Aug. 14, 2014.
Russian Office Action dated Jul. 14, 2016 for corresponding Application No. 2014135386.
Office Action for corresponding Russian application No. 2014135380 dated Aug. 8, 2016 and English translation thereof.
U.S. Office Action U.S. Appl. No. 15/049,573 dated Aug. 26, 2016.
Office Action for corresponding Chinese application No. 201380018578.3 dated Aug. 23, 2016 and English translation thereof.
International Preliminary Report on Patentability for PCT/US2013/024229 dated Aug. 14, 2014.
European Search Report dated May 29, 2015 issued in corresponding European Application No. 13744145.7.
Office Action for corresponding Chinese application No. 201380018578.3 dated Dec. 25, 2015 and English Translation thereof.
New Zealand Office Action dated Jun. 20, 2016 for corresponding NZ Application No. 720667.
Office Action for corresponding Japanese application No. 2014-555720 dated Jan. 10, 2017 and English Translation thereof.
European Search Report dated Dec. 23, 2016 issued in corresponding European Application No. 16165056.9.
Australian Notice of Acceptance for Patent Application No. 2013214987 dated Jan. 24, 2017.
New Zealand First Examination Report for IP No. 627444 dated Feb. 24, 2015.
Australian Notice of Acceptance for Patent Application No. 2013214987 dated Jan. 24, 2017.
Australian Examination Report for Patent Application No. 2013214987 dated Oct. 14, 2016.
Australian Examination Report for Patent Application No. 2013214997 dated Sep. 6, 2016.
New Zealand Examination Report for IP No. 627444 dated Feb. 24, 2015.
New Zealand Examination Report for IP No. 627439 dated Feb. 24, 2015.
New Zealand First Examination Report for IP No. 720667 dated Jun. 20, 2016.
Australian Examination Report for Patent Application No. 2013214991 dated Oct. 20, 2016.
Australian Examination Report for Patent Application No. 2013214998 dated Sep. 27, 2016.
Office Action for corresponding Chinese application No. 201380017766.4 dated Feb. 17, 2017 with English translation thereof.
New Zealand First Examination Report for IP No. 714217 dated Dec. 4, 2015.
European Search Report for Application No. 16165066.8 dated Mar. 16, 2017.
Office Action for corresponding Chinese Application No. 201380007585.3 dated May 11, 2017 and English translation thereof.
European Search Report for corresponding application No. 16165071.8 dated Apr. 7, 2017.
Office Action for corresponding Chinese application No. 201380018495.4 dated Mar. 8, 2017 and English translation thereof.
Office Action for corresponding Ukranian Application No. a201409540 dated Jun. 2, 2017 and English translation thereof.
Office Action for corresponding Ukranian Application No. a201409539 dated Jun. 9, 2017 and English translation thereof.
Office Action for corresponding European Application No. 13744145.7-1664 dated Jun. 12, 2017.
Office Action for corresponding European Application No. 13744358.6-1664 dated Jun. 12, 2017.
Office Action for corresponding European Application No. 13742632.5-1664 dated Jun. 12, 2017.
Office Action for corresponding European Application No. 13744358.6 dated Jun. 12, 2017.
Office Action for corresponding European Application No. 13743475.9-1614 dated Jul. 4, 2017.
Office Action for corresponding Ukrainian Application No. a201409537 dated Jul. 25, 2017.
United States Office Action for corresponding U.S. Appl. No. 15/065,422 dated Sep. 5, 2017.
Office Action for corresponding Chinese Application No. 201380007585.3 dated Sep. 1, 2017, English translation thereof.

(56) References Cited

OTHER PUBLICATIONS

Office Action for corresponding Japanese Application No. 2014-555720 dated Oct. 6, 2017 and English translation thereof.
Office Action for corresponding Japanese Application No. 2014-555726 dated Oct. 5, 2017 and English translation thereof.
Office Action for corresponding European Application No. 16 165 056.9 and dated Aug. 9, 2017.
Office Action for corresponding Morrocan Application No. 37286 dated Oct. 3, 2017 and English translation thereof.
Office Action for corresponding Morrocan Application No. 37289 dated Oct. 4, 2017 and English translation thereof.
Office Action for corresponding Morroccan Application No. 37289 dated Oct. 4, 2017 and English translation thereof.
Office Action for corresponding U.S. Appl. No. 15/683,135 dated Nov. 9, 2017.
Office Action for corresponding European Application No. 13744145.7-1664 dated Nov. 8, 2017.
Office Action for corresponding U.S. Appl. No. 15/339,005 dated Sep. 28, 2017.
Office Action for corresponding Ukrainian Application No. a201409539 dated Nov. 29, 2017 and English translation thereof.
Office Action for corresponding Chinese Office Action Application No. 201380018495.4 dated Aug. 12, 2016 and English Translation thereof.
Office Action for Corresponding U.S. Appl. No. 13/741,267 dated Nov. 4, 2015.
Office Action for Corresponding U.S. Appl. No. 13/741,267 dated Mar. 9, 2016.
Office Action for Corresponding U.S. Appl. No. 13/741,267 dated Oct. 6, 2016.
Office Action for Corresponding U.S. Appl. No. 13/741,267 dated Jan. 26, 2017.
Notice of Allowance for Corresponding U.S. Appl. No. 13/741,267 dated Jul. 25, 2017.
Office Action issued Mar. 15, 2018 in Malaysian Application No. PI 2014002250.
Office Action issued Apr. 26, 2018 in U.S. Appl. No. 15/911,520.
Office Action for corresponding Malaysian Application No. PI2014002168 dated Mar. 15, 2018.
Office Action for corresponding Malaysian Application No. PI2014002250 dated Mar. 15, 2018.
Office Action for corresponding Malaysian Application No. PI 2014002169 dated Mar. 30, 2018.
Re-examination Notice for corresponding Chinese Application No. 201380007585.3 dated May 21, 2018.
Office Action for corresponding U.S. Appl. No. 15/911,520 dated.
Final Office Action for corresponding U.S. Appl. No. 15/911,520 dated Aug. 9, 2018.
Israeli Office Action for corresponding Israeli Application No. 233885 dated Nov. 6, 2018 and English translation thereof.
U.S. Office Action dated Dec. 18, 2018 for corresponding U.S. Appl. No. 15/590,387.
"What is Vaping", Dr. Linda Richter, Center on Addiction, 2018 [online], retrieved from the Internet, [retrieved Dec. 10, 2018], <URL: https://www.centeronaddiction.org/e-cigarettes/recreational-vaping/what-vaping>. (Year: 2018).
Definition of aerosol, Merriam-Webster [online], retrieved Jun. 8, 2017, [retrieved from the Internet], <URL: https://www.merriam-webster.com/dictionary/aerosol>. (Year: 2017).
Israeli Office Action for corresponding Israeli Application No. 233884 dated Nov. 6, 2018 and English translation thereof.
United States Office Action for corresponding U.S. Appl. No. 15/590,456 dated Jan. 18, 2019.
Office Action for corresponding U.S. Appl. No. 15/911,520 dated Jan. 30, 2019.
Chinese Reexamination Notice for corresponding Application No. 201380017766.4 dated Jan. 28, 2019, English translation thereof.
Indian Examination Report for corresponding Application No. 6416/CHENP/2014 dated Jan. 30, 2019, English translation thereof.
Indian Examination Report for corresponding Application No. 6434/CHENP/2014 dated Mar. 13, 2019, English translation thereof.
United States Office Action for corresponding U.S. Appl. No. 15/683,135 dated Mar. 20, 2019.
European Office Action for corresponding Application No. 13744358.6-1122 dated Mar. 1, 2019.
European Office Action for corresponding Application No. 16165066.8-1122 dated Mar. 18, 2019.
Indian Office Action for corresponding Application No. 5797/CHENP/2014 dated Apr. 5, 2019.
United States Notice of Allowance for corresponding U.S. Appl. No. 15/590,456 dated May 8, 2019.
Final Office Action for corresponding U.S. Appl. No. 15/911,520 dated May 13, 2019.
European Office Action for corresponding Application No. 16165056.9-1122, dated May 14, 2019.
European Office Action for corresponding Application No. 13743632.5-1122, dated May 15, 2019.
Malaysian Substantive Examination Adverse Report for corresponding Application No. PI2014002169 dated Jun. 13, 2019.
United States Office Action for U.S. Appl. No. 15/911,520, dated Nov. 21, 2019.
United States Notice of Allowance for U.S. Appl. No. 15/590,456, dated May 8, 2019.
United States Office Action for U.S. Appl. No. 15/857,836, dated Feb. 6, 2020.
United States Final Office Action for U.S. Appl. No. 15/911,520, dated Apr. 13, 2020.
United States Office Action for U.S. Appl. No. 15/911,520, dated Apr. 13, 2020.
United States Notice of Allowance for U.S. Appl. No. 15/857,836, dated May 18, 2020.
United States Notice of Allowance for U.S. Appl. No. 15/911,520, dated Aug. 5, 2020.
Non-Final Office Action issued Sep. 24, 2020 in U.S. Appl. No. 16/784,357.
Communication pursuant to Article 94(3) EPC issued Oct. 16, 2020 in European Application No. 13 743 632.5.
European Office Action dated Oct. 21, 2020 for corresponding European Application No. 16165056.9.
European Examination Report dated Nov. 12, 2020 for corresponding European Application No. 16165066.8.
Israeli Official Notification dated Dec. 27, 2020 for corresponding Israeli Application No. 274421, and English-language translation thereof.
Israeli Official Notification dated Dec. 27, 2021 for corresponding Israeli Application No. 274419, and English-language translation thereof.
U.S. Office Action dated Oct. 29, 2021 for corresponding U.S. Appl. No. 16/784,357.
U.S. Office Action dated Feb. 3, 2022 for corresponding U.S. Appl. No. 16/784,357.
U.S. Office Action dated Mar. 24, 2022 for corresponding U.S. Appl. No. 17/084,003.
U.S. Notice of Allowance dated Jul. 1, 2022 for corresponding U.S. Appl. No. 17/084,003.
European Communication dated Jun. 24, 2022 for corresponding European Application No. 16165056.9.
Extended European Search Report dated Oct. 7, 2022 for corresponding European Application No. 22179927.3.
U.S. Office Action dated Jan. 23, 2023 for corresponding U.S. Appl. No. 16/784,357.
Notice of Allowance dated Apr. 5, 2023 issued in related U.S. Appl. No. 17/215,254.
Office Action dated Apr. 24, 2023 issued in related European Patent Application No. 16165056.9.
Brief Communication, "Letter from the Opponent," dated Feb. 28, 2023 issued in related European Patent Application No. 13744143.2.
Maciej L. Goniewicz, Ph.d., et al., "Nicotine Levels in Electronic Cigarettes," Nicotine & Tobacco Research, vol. 15, No. 1 (Jan. 2013), pp. 158-166.

(56) References Cited

OTHER PUBLICATIONS

"Heating element," in "Wikipedia," revision of Jan. 16, 2012, available online: https://en.wikipedia.org/w/index.php?title=Heating_element&oldid=471699392, retrieved on Apr. 28, 2023.
Post "Kanthal or Nichrome" in the "E-Cigarette Forum" of Apr. 20, 2012, available online: https://www.e-cigarette-forum.com/threads/kanthal-or-nichrome.289315/, retrieved on Apr. 28, 2023.
Screenshot of p. 1 of Post "Kanthal or Nichrome" in the "E-Cigarette Forum" of Apr. 20, 2012, available online: https://www.e-cigarette-forum.com/threads/kanthal-or-nichrome.289315/, retrieved on Apr. 20, 2023.
Notice of Opposition dated May 9, 2023 issued in related European patent application No. 13743632.5.
Office Action dated Sep. 19, 2024 issued in U.S. Appl. No. 17/970,135.
Notice of Allowance dated Dec. 4, 2024 issued in U.S. Appl. No. 16/784,357.
Notice of Allowance dated Jan. 15, 2025 issued in U.S. Appl. No. 17/970,135.

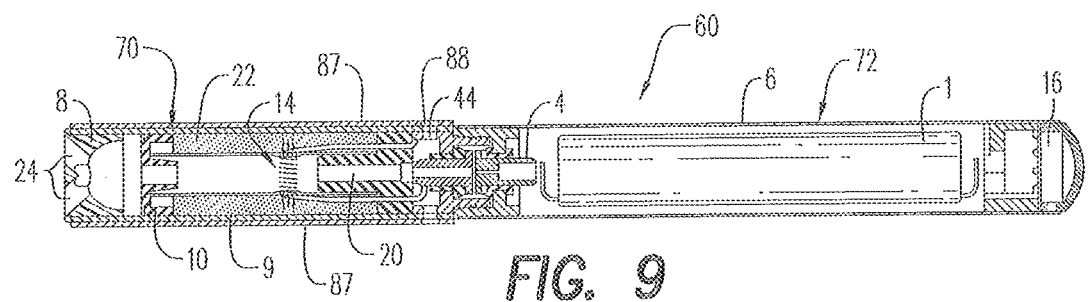
FIG. 9
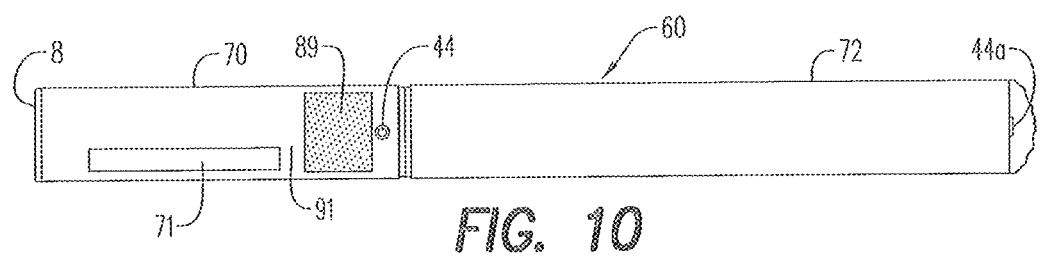
FIG. 10
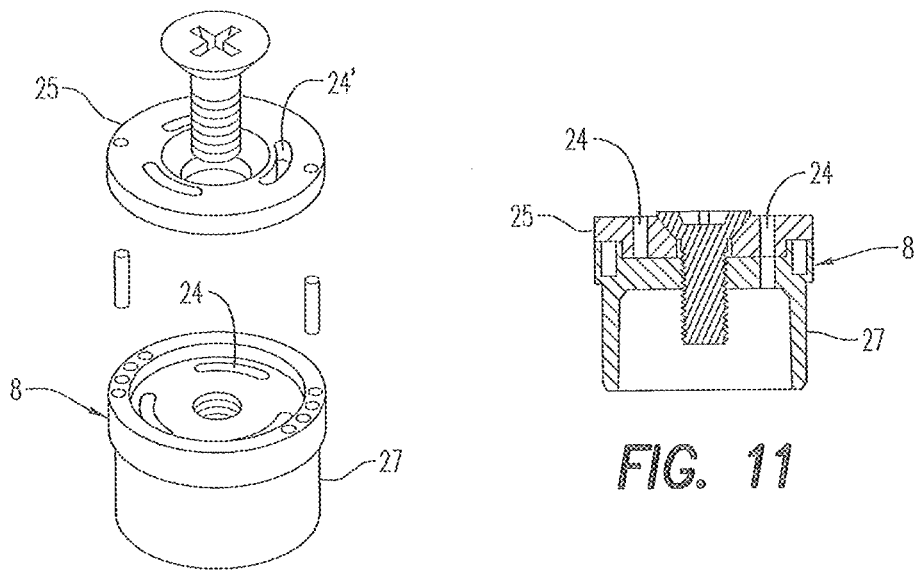
FIG. 11
FIG. 12

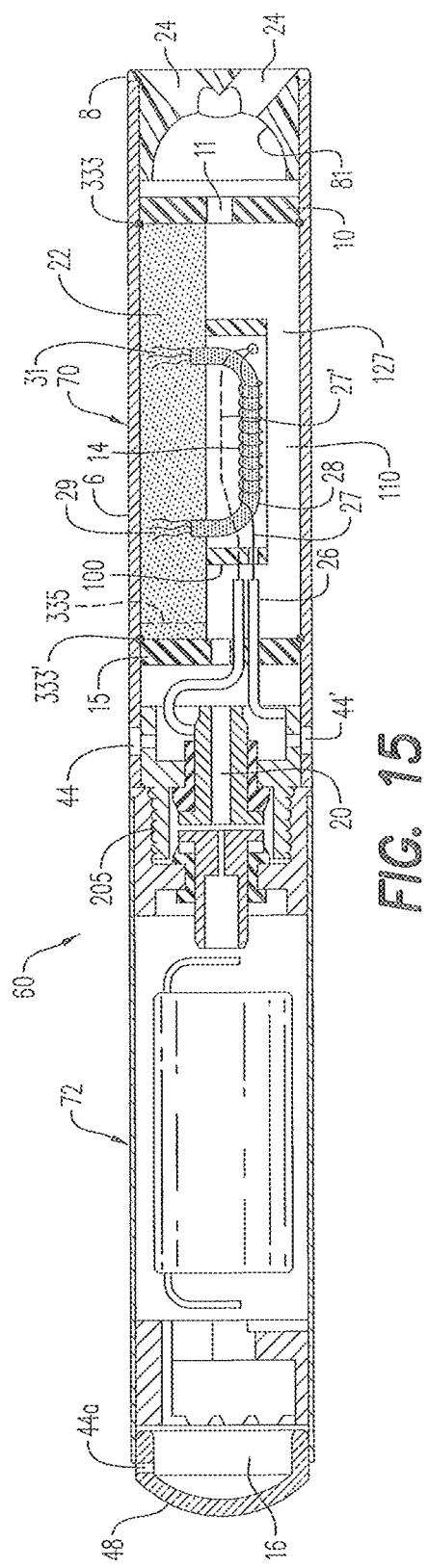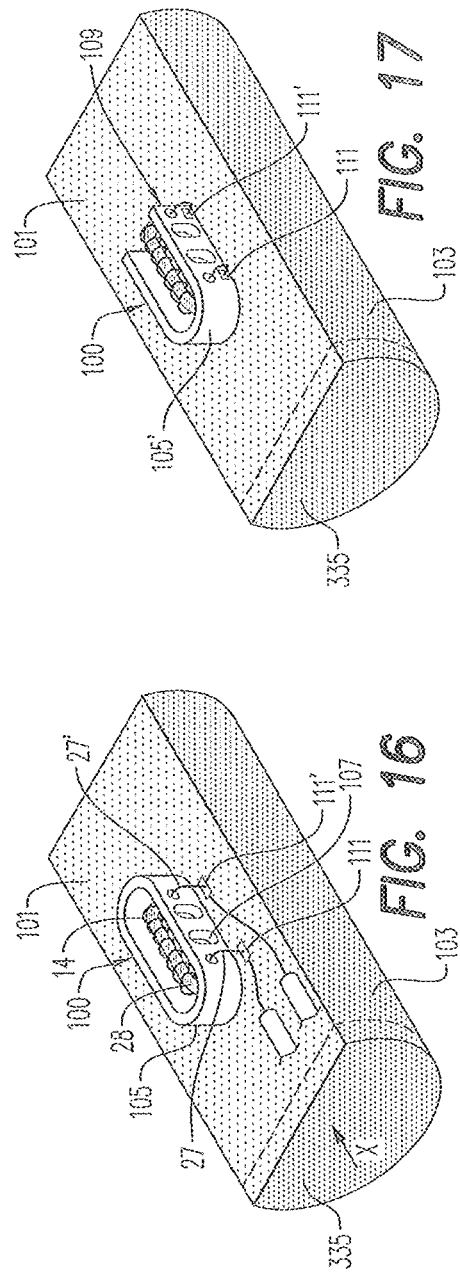

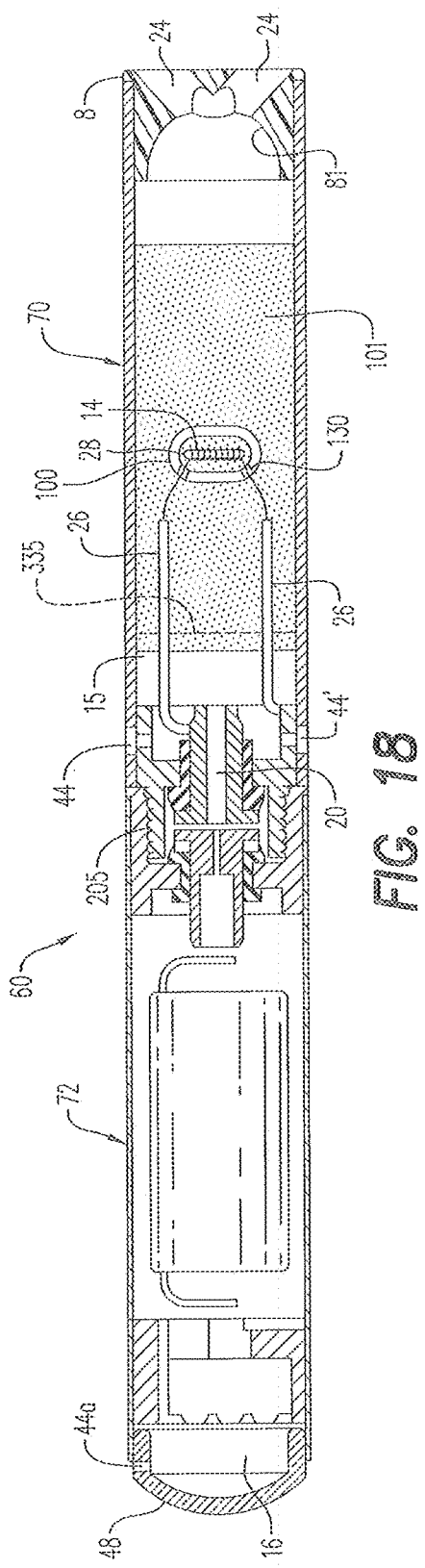
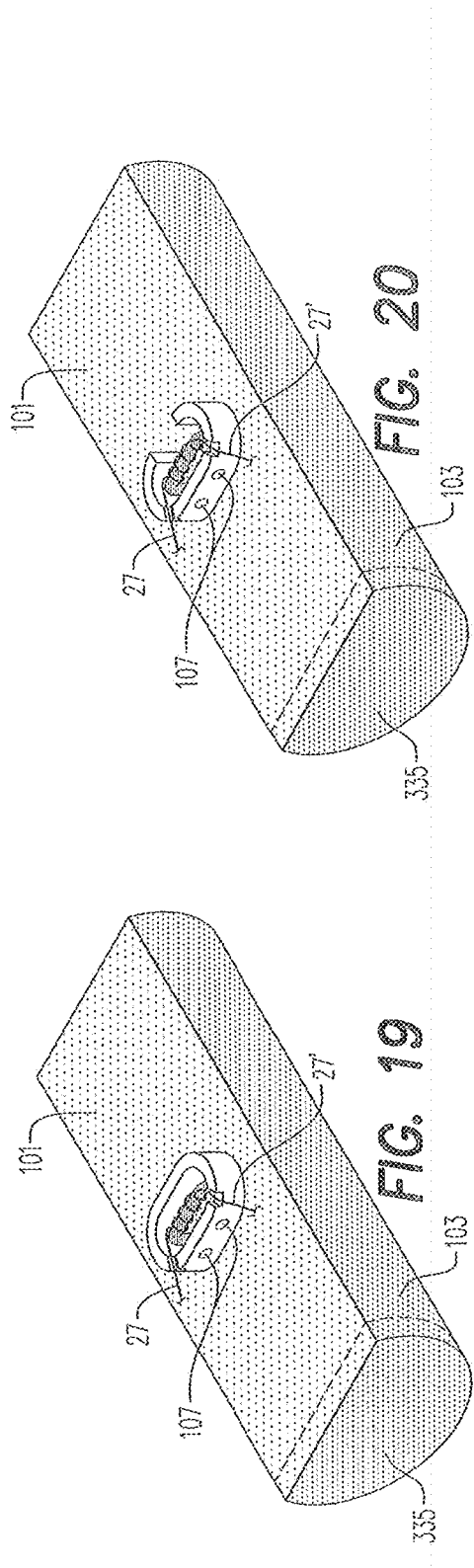

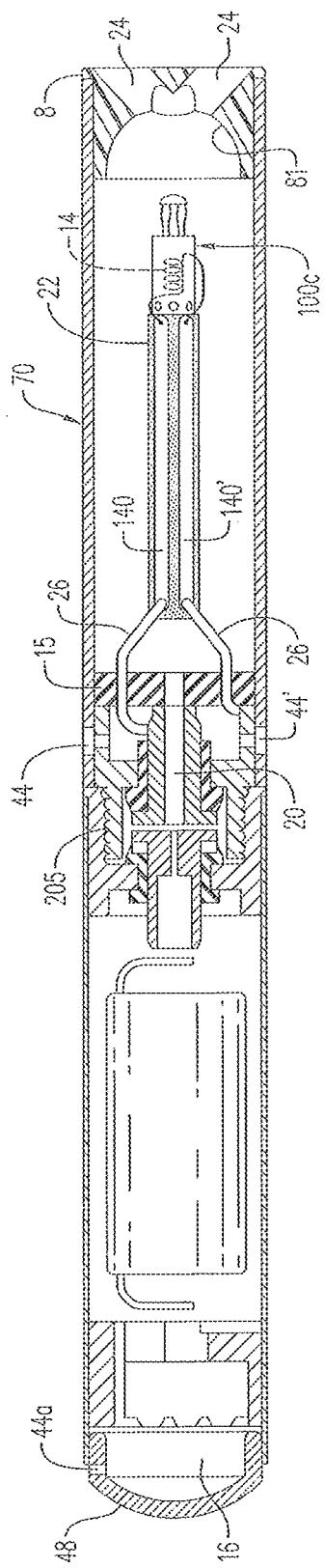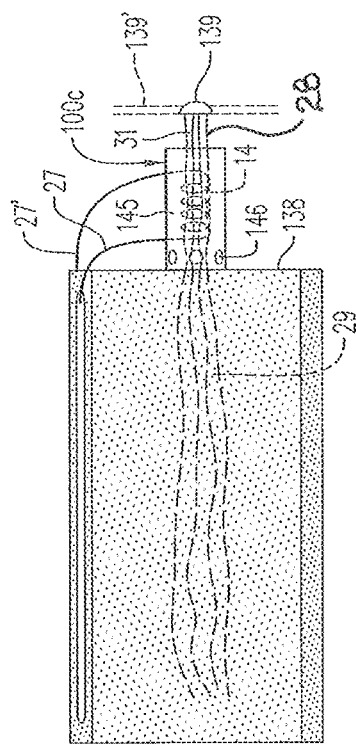
FIG. 24
FIG. 25

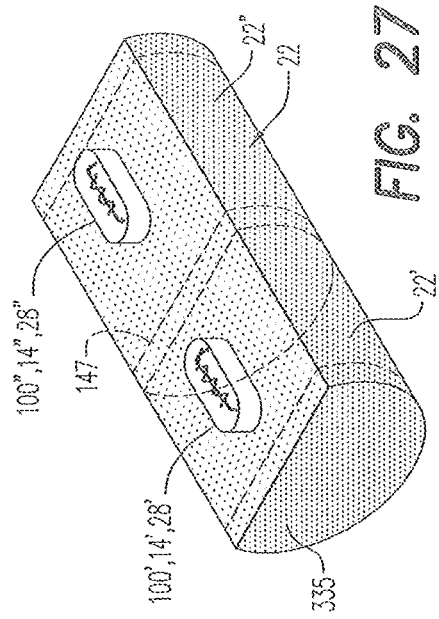
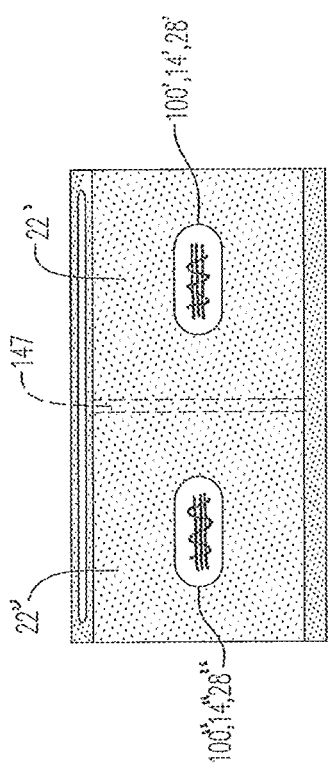

ELECTRONIC CIGARETTE

CROSS REFERENCE TO RELATED APPLICATION

This application is a continuation application of U.S. application Ser. No. 17/215,254, filed Mar. 29, 2021, which is a divisional application of U.S. application Ser. No. 16/106,049, filed Aug. 21, 2018, which is a divisional application of U.S. application Ser. No. 15/065,422, filed Mar. 9, 2016; which is a Divisional of U.S. application Ser. No. 13/756,127, filed Jan. 31, 2013; which claims the benefit of priority under 35 U.S.C. § 119(e) to U.S. Provisional Application No. 61/593,004, filed on Jan. 31, 2012, the entire contents of each of which are incorporated herein by reference.

SUMMARY OF SELECTED FEATURES

An electronic cigarette includes a heater which vaporizes liquid material to produce an aerosol and an airflow diverter for abating the tendency of incoming air to reduce heater performance and aerosol output due to its cooling effect upon the heater during a puff. The electronic cigarette can also include a mouth end insert including at least two diverging outlets.

BRIEF DESCRIPTION OF THE DRAWINGS

FIG. 9 is a cross-sectional view of an electronic cigarette according to the first embodiment and further including a sleeve assembly.

FIG. 10 is a top view of an electronic cigarette including an aroma strip on an outer surface thereof.

FIG. 11 is a cross-sectional view of a second embodiment of a mouth end insert for use with the electronic cigarettes of FIGS. 1, 4, 6 and 8.

FIG. 12 is an exploded view of the mouth end insert of FIG. 11.

FIG. 15 is a cross-sectional view of an embodiment wherein an electronic cigarette includes an air flow diverter.

FIG. 16 is an enlarged view of an air flow diverter and tank reservoir of the electronic cigarette of FIG. 15.

FIG. 17 is an enlarged view of an alternate air flow diverter and tank reservoir of the electronic cigarette of FIG. 15.

FIG. 18 is a cross-sectional view of an embodiment wherein an electronic cigarette includes an air flow diverter.

FIG. 19 is an enlarged view of an air flow diverter and tank reservoir of the electronic cigarette of FIG. 18.

FIG. 20 is enlarged views of an alternate air flow diverter and tank reservoir of the electronic cigarette of FIG. 18.

FIG. 24 is a cross-sectional top view of an embodiment wherein an electronic cigarette includes a tank reservoir and an air flow diverter disposed about a longitudinally extending wick.

FIG. 25 is a side view of the tank reservoir, the longitudinally extending wick and the air flow diverter of the electronic cigarette of FIG. 24.

FIG. 26 is a side view of an alternate tank reservoir having more than one liquid compartment, each with its own wick, heater and air flow diverter.

FIG. 27 is a perspective view of another alternate tank reservoir having more than one liquid compartment, each with its own wick, heater and the air flow diverter.

DETAILED DESCRIPTION

Figure 1:
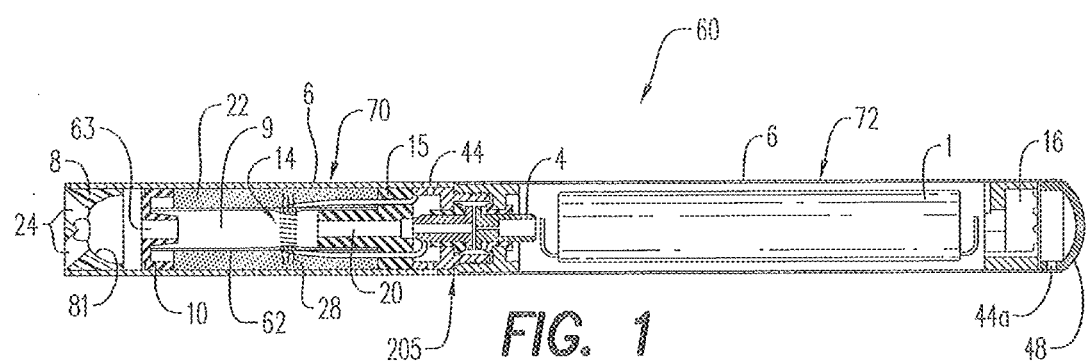
FIG. 1 is a cross-sectional view of an electronic cigarette according to a first embodiment wherein the mouth end insert includes diverging outlets.

An electronic cigarette provides improved aerosol output and/or better mouthfeel by utilizing one or more of a mouth end insert including at least two off-axis, preferably diverging outlets, at least one air flow diverter and/or alternative materials for the construction of the electronic cigarette.

Not wishing to be bound by theory, the use of a mouth end insert having at least two off-axis, preferably diverging outlets allows for greater distribution of aerosol into a smoker's mouth so as to provide a fuller mouth feel. The mouth end insert also provides an impaction surface for collecting unaerosolized liquid droplets which prevents such liquid droplets from exiting the mouth end insert in a non-aerosolized form. The impaction surface of the mouth end insert also acts to intensify heat due to droplets striking the surface during smoking.

Moreover, while not wishing to be bound by theory, the use of an air flow diverter acts to slow the air flow and/or redirect at least some air flow around portions of the heater so as to abate the tendency of drawn airflow to cool the heater during increased draw on the electronic cigarette. It is believed that by reducing the cooling effect on the heater, it will provide greater aerosol output during longer and/or stronger draws on an electronic cigarette, as expected by the smoker.

As shown in FIGS. 1, 4, 6, 8, 9 and 13, a novel electronic cigarette 60 comprises a replaceable cartridge (or first section) 70 and a reusable fixture (or second section) 72, which are coupled together at a threaded connection 205 or by other convenience such as a snug-fit, detent, clamp and/or clasp. The first section 70 includes an outer tube 6 (or casing) extending in a longitudinal direction and an inner tube 62 coaxially positioned within the outer tube or casing 6. The second section 72 can also include an outer tube 6 (or casing) extending in a longitudinal direction. In an alternative embodiment, the outer tube 6 can be a single tube housing both the first section 70 and the second section 72 and the entire electronic cigarette 60 can be disposable.

In an embodiment, the electronic cigarette 60 can also include a central air passage 20 in an upstream seal 15. The central air passage 20 opens to the inner tube 62. Moreover, the electronic cigarette 60 includes a liquid supply reservoir 22. The liquid supply comprises a liquid material and optionally a liquid storage medium 21 operable to store the liquid material therein. In an embodiment, the liquid supply reservoir 22 is contained in an outer annulus between the outer tube 6 and the inner tube 62. The annulus is sealed at an upstream end by the seal 15 and by a liquid stopper 10 at a downstream end so as to prevent leakage of the liquid material from the liquid supply reservoir 22.

In an embodiment, a heater 14 is also contained in the inner tube 62 downstream of and in spaced apart relation to the central air passage 20. The heater 14 can be in the form of a wire coil, a planar body, a ceramic body, a single wire, a cage of resistive wire or any other suitable form. A wick 28 is in communication with the liquid material in the liquid supply reservoir 22 and in communication with the heater 14 such that the wick 28 disposes liquid material in proximate relation to the heater 14. The wick 28 may be constructed of a fibrous and flexible material. The wick 28 preferably comprises at least one filament having a capacity to draw a liquid, more preferably the wick 28 comprises a bundle of filaments which may comprise glass (or ceramic) filaments and most preferably a bundle comprising a group of windings of glass filaments, preferably three of such windings, all which arrangements are capable of drawing liquid via capillary action via interstitial spacings between the filaments. A power supply 1 in the second section 72 is operable to apply voltage across the heater 14. The electronic cigarette 60 also includes at least one air inlet 44 operable to deliver air to the central air passage 20 and/or other portions of the inner tube 62.

Figure 7:
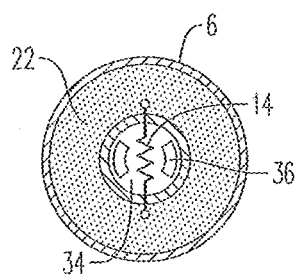
FIG. 7 is a cross-sectional view along line A-A of the electronic cigarette of FIG. 6.
Figure 8:
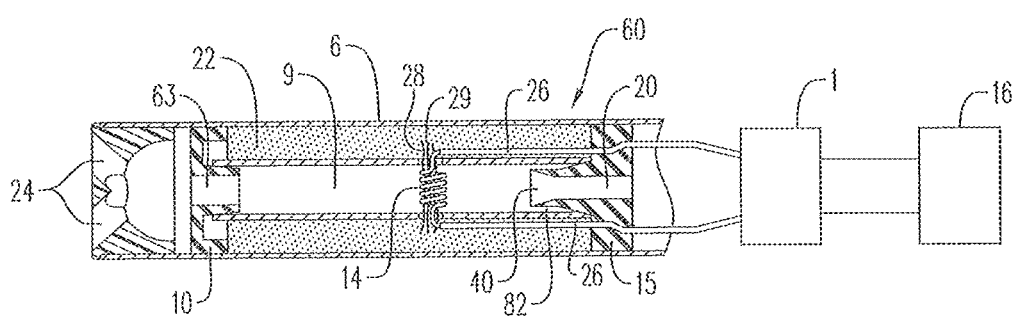
FIG. 8 is a cross-sectional view of an embodiment wherein an electronic cigarette includes an air flow diverter.
Figures 13, 14:
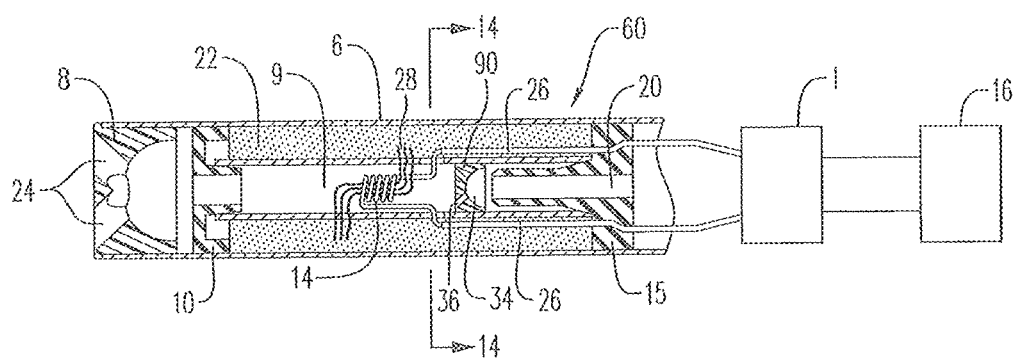
FIG. 13 is a cross-sectional view of an embodiment wherein an electronic cigarette includes an air flow diverter.
FIG. 14 is a cross-sectional view along line A'-A' of the electronic cigarette of FIG. 13.

The electronic cigarette 60 further includes a mouth end insert 8 having at least two off-axis, preferably diverging outlets 24. The mouth end insert 8 is in fluid communication with the central air passage 20 via the interior of inner tube 62 and a central passage 63, which extends through the stopper 10. Moreover, as shown in FIGS. 7 and 8, the heater 14 preferably extends in a direction transverse to the longitudinal direction and heats the liquid material to a temperature sufficient to vaporize the liquid material and form an aerosol. In other embodiments, other orientations of the heater 14 are contemplated. For example, as shown in FIG. 13, the heater 14 and the heated portion of the wick 28 can be arranged longitudinally within the inner tube 62. Preferably, as shown, the heater 14 is arranged centrally within the inner tube 62. However, in other embodiments the heater 14 can be arranged adjacent an inner surface of the inner tube 62.

Referring now to FIG. 1, the wick 28, liquid supply reservoir 22 and mouth end insert 8 are contained in the cartridge 70 and the power supply 1 is contained in the second section 72. In one embodiment, the first section (the cartridge) 70 is disposable and the second section (the fixture) 72 is reusable. The sections 70, 72 can be attached by a threaded connection 205 whereby the downstream section 70 can be replaced when the liquid supply reservoir 22 is used up. Having a separate first section 70 and second section 72 provides a number of advantages. First, if the first section 70 contains the at least one heater 14, the liquid supply reservoir 22 and the wick 14, all elements which are potentially in contact with the liquid are disposed of when the first section 70 is replaced. Thus, there will be no cross-contamination between different mouth end inserts 8, for example, when using different liquid materials. Also, if the first section 70 is replaced at suitable intervals, there is little chance of the heater becoming clogged with liquid. Optionally, the first section 70 and the second section 72 are arranged to releasably lock together when engaged.

In one embodiment, as shown in FIG. 10, the outer tube 6 can include a clear (transparent) window 71 formed of a transparent material so as to allow a smoker to see the amount of liquid material remaining in the liquid supply reservoir 22. The clear window 71 can extend at least a portion of the length of the first section 70 and can extend fully or partially about the circumference of the first section 70. In another embodiment, the outer tube 6 can be at least partially formed of a transparent material so as to allow a smoker to see the amount of liquid material remaining in the liquid supply reservoir 22.

In an embodiment, the at least one air inlet 44 includes one or two air inlets 44, 44'. Alternatively, there may be three, four, five or more air inlets. Preferably, if there is more than one air inlet 44, 44', the air inlets 44, 44' are located at different locations along the electronic cigarette 60. For example, as shown in FIG. 1, an air inlet 44*a* can be positioned at the upstream end of the cigarette adjacent the puff sensor 16 such that the puff sensor supplies power to the heater upon sensing a puff by the smoker. Air inlet 44*a* should communicate with the mouth end insert 8 so that a draw upon the mouth end insert activates the puff sensor. The air from the air inlet 44*a* can then flow along the battery and to the central air passage 20 in the seal 15 and/or to other portions of the inner tube 62 and/or outer tube 6. At least one additional air inlet 44, 44' can be located adjacent and upstream of the seal 15 or at any other desirable location. Altering the size and number of air inlets 44, 44' can also aid in establishing the resistance to draw of the electronic cigarette 60.

In an embodiment, the heater 14 is arranged to communicate with the wick 28 and to heat the liquid material contained in the wick 28 to a temperature sufficient to vaporize the liquid material and form an aerosol.

The heater 14 is preferably a wire coil surrounding wick 28. Examples of suitable electrically resistive materials include titanium, zirconium, tantalum and metals from the platinum group. Examples of suitable metal alloys include stainless steel, nickel-, cobalt-, chromium-, aluminium-titanium-zirconium-, hafnium-, niobium-, molybdenum-, tantalum-, tungsten-, tin-, gallium-, manganese- and iron-containing alloys, and super-alloys based on nickel, iron, cobalt, stainless steel. For example, the heater can be formed of nickel aluminides, a material with a layer of alumina on the surface, iron aluminides and other composite materials, the electrically resistive material may optionally be embedded in, encapsulated or coated with an insulating material or vice-versa, depending on the kinetics of energy transfer and the external physicochemical properties required. Preferably, the heater 14 comprises at least one material selected from the group consisting of stainless steel, copper, copper alloys, nickel-chromium alloys, superalloys and combinations thereof. In an embodiment, the heater 14 is formed of nickel-chromium alloys or iron-chromium alloys. In one embodiment, the heater 14 can be a ceramic heater having an electrically resistive layer on an outside surface thereof.

In another embodiment, the heater 14 may be constructed of an iron-aluminide (e.g., FeAl or $Fe_3Al$), such as those described in commonly owned U.S. Pat. No. 5,595,706 to Sikka et al. filed Dec. 29, 1994, or nickel aluminides (e.g., $Ni_3Al$). Use of iron-aluminides is particularly advantageous in that they exhibit high resistivity. FeAl exhibits a resistivity of approximately 180 micro-ohms, whereas stainless steel exhibits approximately 50 to 91 micro-ohms. The higher resistivity lowers current draw or load on the power source (battery) 1.

In one embodiment, the heater 14 comprises a wire coil which at least partially surrounds the wick 28. In that embodiment, preferably the wire is a metal wire and/or the heater coil that extends partially along the length of the wick 28. The heater coil may extend fully or partially around the circumference of the wick 28. In another embodiment, the heater coil is not in contact with the wick 28.

Preferably, the heater 14 heats liquid in the wick 28 by thermal conduction. Alternatively, heat from the heater 14 may be conducted to the liquid by means of a heat conductive element or the heater 14 may transfer heat to the incoming ambient air that is drawn through the electronic cigarette 60 during use, which in turn heats the liquid by convection.

In one embodiment, the wick comprises a ceramic material or ceramic fibers. As noted above, the wick 28 is at least partially surrounded by the heater 14. Moreover, in an embodiment, the wick 28 extends through opposed openings in the inner tube 62 such that end portions 29, 31 of the wick 28 are in contact with the liquid supply reservoir 22.

Preferably, the wick 28 may comprise a plurality or bundle of filaments. The filaments may be generally aligned in a direction transverse to the longitudinal direction of the electronic cigarette. In one embodiment, the structure of the wick 28 is formed of ceramic filaments capable of drawing liquid via capillary action via interstitial spacings between the filaments to the heater 14. The wick 28 can include filaments having a cross-section which is generally cross-shaped, clover-shaped, Y-shaped or in any other suitable shape.

Preferably, the wick 28 includes any suitable material or combination of materials. Examples of suitable materials are glass filaments and ceramic or graphite based materials. Moreover, the wick 28 may have any suitable capillarity accommodate aerosol generating liquids having different liquid physical properties such as density, viscosity, surface tension and vapor pressure. The capillary properties of the wick 28, combined with the properties of the liquid, ensure that the wick 28 is always wet in the area of the heater 14 to avoid overheating of the heater 14.

Instead of using a wick, the heater can be a porous material of sufficient capillarity and which incorporates a resistance heater formed of a material having a high electrical resistance capable of generating heat quickly.

In one embodiment, the wick 28 and the fibrous medium 21 of the liquid supply reservoir 22 are constructed from an alumina ceramic. In another embodiment, the wick 28 includes glass fibers and the fibrous medium 21 includes a cellulosic material or polyethylene terephthalate.

In an embodiment, the power supply 1 includes a battery arranged in the electronic cigarette 60 such that the anode is downstream of the cathode. A battery anode connector 4 contacts the downstream end of the battery. The heater 14 is connected to the battery by two spaced apart electrical leads 26 (shown in FIGS. 4, 6 and 8).

Preferably, the connection between the uncoiled, end portions 27, 27' (see FIG. 5) of the heater 14 and the electrical leads 26 are highly conductive and temperature resistant while the heater 14 is highly resistive so that heat generation occurs primarily along the heater 14 and not at the contacts.

The battery can be a Lithium-ion battery or one of its variants, for example a Lithium-ion polymer battery. Alternatively, the battery may be a Nickel-metal hydride battery, a Nickel cadmium battery, a Lithium-manganese battery, a Lithium-cobalt battery or a fuel cell. In that case, preferably, the electronic cigarette 60 is usable by a smoker until the energy in the power supply is depleted. Alternatively, the power supply 1 may be rechargeable and include circuitry allowing the battery to be chargeable by an external charging device. In that case, preferably the circuitry, when charged, provides power for a pre-determined number of puffs, after which the circuitry must be re-connected to an external charging device.

Preferably, the electronic cigarette 60 also includes control circuitry including a puff sensor 16. The puff sensor 16 is operable to sense an air pressure drop and initiate application of voltage from the power supply 1 to the heater 14. The control circuitry can also include a heater activation light 48 operable to glow when the heater 14 is activated. Preferably, the heater activation light 48 comprises an LED 48 and is at an upstream end of the electronic cigarette 60 so that the heater activation light 48 takes on the appearance of a burning coal during a puff. Moreover, the heater activation light 48 can be arranged to be visible to the smoker. In addition, the heater activation light 48 can be utilized for cigarette system diagnostics. The light 48 can also be configured such that the smoker can activate and/or deactivate the light 48 for privacy, such that the light 48 would not activate during smoking if desired.

Preferably, the at least one air inlet 44a is located adjacent the puff sensor 16, such that the puff sensor 16 senses air flow indicative of a smoker taking a puff and activates the power supply 1 and the heater activation light 48 to indicate that the heater 14 is working.

A control circuit is integrated with the puff sensor 16 and supplies power to the heater 14 responsive to the puff sensor 16, preferably with a maximum, time-period limiter.

Alternatively, the control circuitry may include a manually operable switch for a smoker to initiate a puff. The time-period of the electric current supply to the heater may be pre-set depending on the amount of liquid desired to be vaporized. The control circuitry is preferably programmable for this purpose. Alternatively, the circuitry may supply power to the heater as long as the puff sensor detects a pressure drop.

Preferably, when activated, the heater 14 heats a portion of the wick 28 surrounded by the heater for less than about 10 seconds, more preferably less than about 7 seconds. Thus, the power cycle (or maximum puff length) can range in period from about 2 seconds to about 10 seconds (e.g., about 3 seconds to about 9 seconds, about 4 seconds to about 8 seconds or about 5 seconds to about 7 seconds).

In an embodiment, the liquid supply reservoir 22 includes a liquid storage medium 21 containing liquid material. In the embodiments shown in FIGS. 1, 4, 6, 8, 9 and 13, the liquid supply reservoir 22 is contained in an outer annulus 62 between inner tube 62 and outer tube 6 and between stopper 10 and the seal 15. Thus, the liquid supply reservoir 22 at least partially surrounds the central air passage 20 and the heater 14 and the wick 14 extend between portions of the liquid supply reservoir 22. Preferably, the liquid storage material is a fibrous material comprising cotton, polyethylene, polyester, rayon and combinations thereof. Preferably, the fibers have a diameter ranging in size from about 6 microns to about 15 microns (e.g., about 8 microns to about 12 microns or about 9 microns to about 11 microns). The liquid storage medium 21 can be a sintered, porous or foamed material. Also preferably, the fibers are sized to be irrespirable and can have a cross-section which has a y shape, cross shape, clover shape or any other suitable shape. In the alternative, the reservoir 22 may comprise a filled tank lacking a fibrous storage medium 21, such as further described with reference to FIGS. 15-26.

Also preferably, the liquid material has a boiling point suitable for use in the electronic cigarette 60. If the boiling point is too high, the heater 14 will not be able to vaporize liquid in the wick 28. However, if the boiling point is too low, the liquid may vaporize without the heater 14 being activated.

The liquid material may include a tobacco-containing material including volatile tobacco flavor compounds which are released from the liquid upon heating. The liquid may also be a tobacco flavor containing material or a nicotine-containing material. Alternatively, or in addition, the liquid may include a non-tobacco material. For example, the liquid may include water, solvents, ethanol, plant extracts and natural or artificial flavors. Preferably, the liquid further includes an aerosol former. Examples of suitable aerosol formers are glycerine and propylene glycol.

Figure 4:
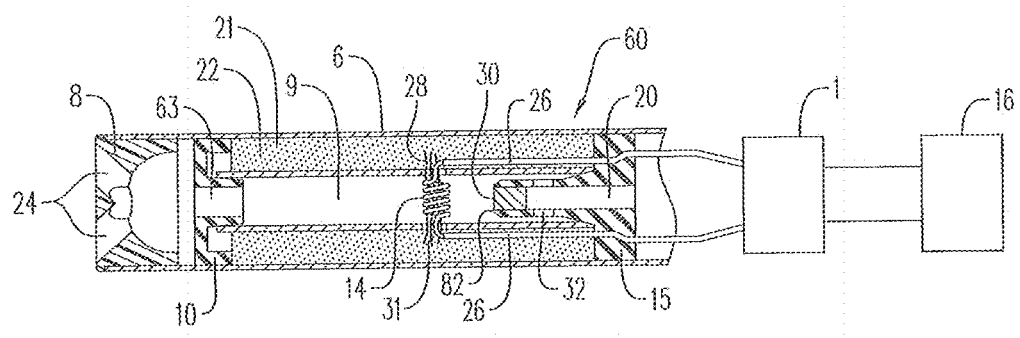
FIG. 4 is a cross-sectional view of an embodiment wherein an electronic cigarette includes an air flow diverter.

In use, liquid material is transferred from the liquid supply reservoir 22 and/or liquid storage medium 21 in proximity of the 14 heater by capillary action in the wick 28. In one embodiment, the wick 28 has a first end portion 29 and a second opposite end portion 31 as shown in FIG. 4. The first end portion 29 and the second end portion 31 extend into opposite sides of the liquid storage medium 21 for contact with liquid material contained therein. Also preferably, the heater 14 at least partially surrounds a central portion of the wick 28 such that when the heater is activated, the liquid in the central portion of the wick 28 is vaporized by the heater 14 to vaporize the liquid material and form an aerosol.

One advantage of an embodiment is that the liquid material in the liquid supply reservoir 22 is protected from oxygen (because oxygen cannot generally enter the liquid storage portion via the wick) so that the risk of degradation of the liquid material is significantly reduced. Moreover, in some embodiments in which the outer tube 6 is not clear, the liquid supply reservoir 22 is protected from light so that the risk of degradation of the liquid material is significantly reduced. Thus, a high level of shelf-life and cleanliness can be maintained.

Figure 2:
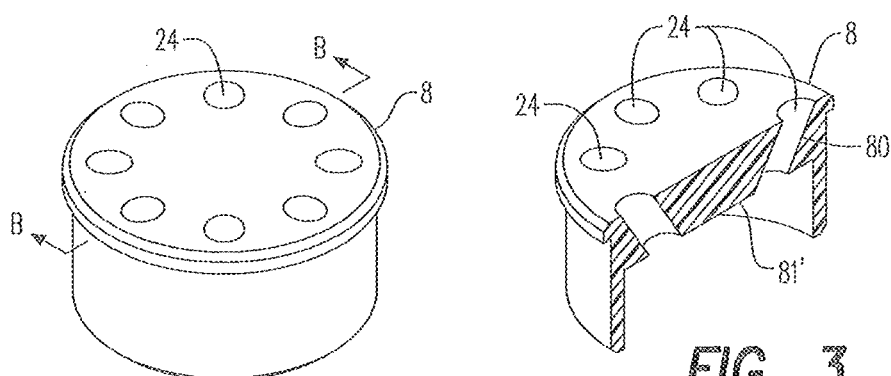
FIG. 2 is a perspective view of a mouth end insert for use with the electronic cigarette of FIG. 1.
Figure 3:
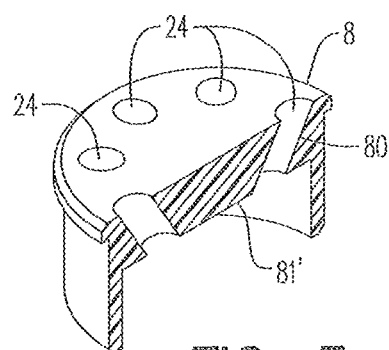
FIG. 3 is a cross-sectional view along line B-B of the mouth end insert of FIG. 2.

As shown in FIGS. 2 and 3, the mouth end insert 8, includes at least two diverging outlets 24 (e.g., 3, 4, 5 or more, preferably 2 to 10 outlets or more, more preferably 2 to 6 outlet passages 24, even more preferably 4 outlet passages 24). Preferably, the outlets 24 of the mouth end insert 8 are located at ends of off-axis passages 80 and are angled outwardly in relation to the longitudinal direction of the electronic cigarette 60 (i.e., divergently). As used herein, the term "off-axis" denotes at an angle to the longitudinal direction of the electronic cigarette. Also preferably, the mouth end insert (or flow guide) 8 includes outlets uniformly distributed around the mouth end insert 8 so as to substantially uniformly distribute aerosol in a smoker's mouth during use. Thus, as the aerosol passes into a smoker's mouth, the aerosol enters the mouth and moves in different directions so as to provide a full mouth feel as compared to electronic cigarettes having an on-axis single orifice which directs the aerosol to a single location in a smoker's mouth.

In addition, the outlets 24 and off-axis passages 80 are arranged such that droplets of unaerosolized liquid material carried in the aerosol impact interior surfaces 81 at mouth end insert and/or interior surfaces of the off-axis passages such that the droplets are removed or broken apart. In an embodiment, the outlets of the mouth end insert are located at the ends of the off-axis passages and are angled at 5 to 60° with respect to the central axis of the outer tube 6 so as to more completely distribute aerosol throughout a mouth of a smoker during use and to remove droplets.

Preferably, each outlet has a diameter of about 0.015 inch to about 0.090 inch (e.g., about 0.020 inch to about 0.040 inch or about 0.028 inch to about 0.038 inch). The size of the outlets 24 and off-axis passages 80 along with the number of outlets can be selected to adjust the resistance to draw (RTD) of the electronic cigarette 60, if desired.

As shown in FIG. 1, an interior surface 81 of the mouth end insert 8 can comprise a generally domed surface. Alternatively, as shown in FIG. 3, the interior surface 81' of the mouth end insert 8 can be generally cylindrical or frustoconical, with a planar end surface. Preferably, the interior surface is substantially uniform over the surface thereof or symmetrical about the longitudinal axis of the mouth end insert 8. However, in other embodiments, the interior surface can be irregular and/or have other shapes.

Preferably, the mouth end insert 8 is integrally affixed within the tube 6 of the cartridge 70. Moreover, the mouth end insert 8 can be formed of a polymer selected from the group consisting of low density polyethylene, high density polyethylene, polypropylene, polyvinylchloride, polyetheretherketone (PEEK) and combinations thereof. The mouth end insert 8 may also be colored if desired.

In an embodiment, the electronic cigarette 60 also includes various embodiments of an air flow diverter or air flow diverter means, which are shown in FIGS. 4, 6, 8, 13, 15-26. The air flow diverter is operable to manage air flow at or about around the heater so as to abate a tendency of drawn air to cool the heater, which could otherwise lead to diminished aerosol output.

Figure 5:
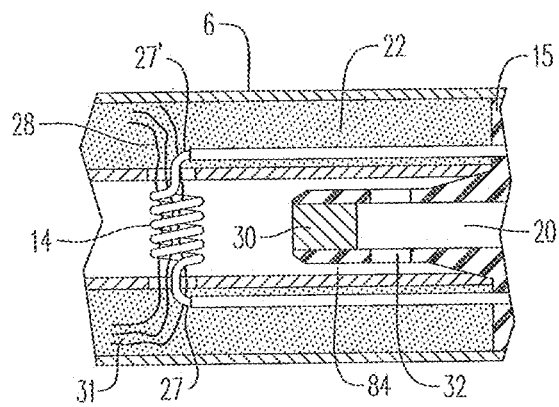
FIG. 5 is an enlarged view of the air flow diverter of the electronic cigarette of FIG. 4.

In one embodiment, as shown in FIGS. 4 and 5, the electronic cigarette 60 can include an air flow diverter comprising an impervious plug 30 at a downstream end 82 of the central air passage 20 in seal 15. Preferably, the central air passage 20 is an axially extending central passage in seal 15, which seals the upstream end of the annulus between the outer and inner tubes 6, 60. The air flow diverter can preferably include at least one radial air channel 32 directing air from the central passage 20 outward toward the inner tube 62 and into an outer air passage 84 defined between an outer periphery of a downstream end portion of the seal 15 and the inner wall of inner tube 62.

Preferably, the diameter of the bore of the central air passage 20 is substantially the same as the diameter of the at least one radial air channel 32. Also preferably, the diameter of the bore of the central air passage 20 and the at least one radial air channel 32 ranges from about 1.5 mm to about 3.5 mm (e.g., about 2.0 mm to about 3.0 mm). Optionally, the diameter of the bore of the central air passage 20 and the at least one radial air channel 32 can be adjusted to control the resistance to draw of the electronic cigarette 60. In use, the air flows into the bore of the central air passage 20, through the at least one radial air channel 32 and into the outer air passage 84 such that a lesser portion of the air flow is directed at a central portion of the heater 14 so as to minimize the aforementioned cooling effect of the airflow on the heater 14 during heating cycles. Thus, incoming air is directed away from the center of the heater 14 and the air velocity past the heater is reduced as compared to when the air flows through a central opening in the seal 15 oriented directly in line with a middle portion of the heater 14.

Figure 6:
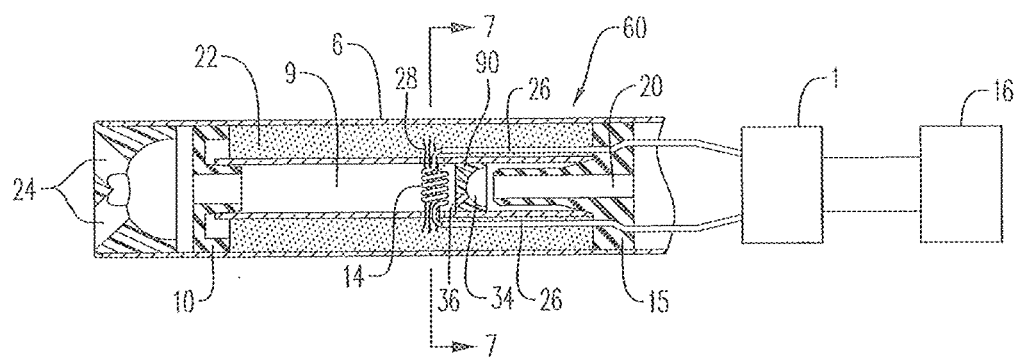
FIG. 6 is a cross-sectional view of an embodiment wherein an electronic cigarette includes an air flow diverter.

In another embodiment, as shown in FIGS. 6 and 7, the air flow diverter can be in the form of a disc 34 positioned between the downstream end of seal 15 and the heater 14. The disc 34 includes at least one orifice 36 in a transverse wall at a downstream end of an outer tubular wall 90. Also preferably, the at least one orifice 36 is off-axis so as to direct incoming air outward towards the inner wall of tube 62. During a puff, the disc 34 is operable to divert air flow away from a central portion of the heater 14 so as to counteract the tendency of the airflow to cool the heater as a result of a strong or prolonged draw by a smoker. Thus, the heater 14 is substantially prevented from cooling during heating cycles so as to prevent a drop in the amount of aerosol produced during a puff.

As shown in FIGS. 13 and 14, the heater 14 is oriented longitudinally within the inner tube 62 and the disc 34 includes at least one orifice 36 arranged to direct air flow non-centrally and/or radially away from the centralized location of the heater 14. In embodiment where the heater 14 is oriented longitudinally within the inner tube 62 and adjacent an inner wall of the inner tube 62, the orifices 36 can be arranged to direct at least a portion of the airflow away from the heater 14 so as to abate the cooling effect of the air flow upon the heater 14 during a power cycle and/or be arranged to decelerate the air flow to achieve the same effect.

In yet another embodiment, as shown in FIG. 8, the air flow diverter comprises a frustoconical section 40 extending from the downstream end 82 of a shortened central air passage 20. By shortening the central passage 20 as compared to other embodiments, the heater 14 is positioned farther away from the central passage 20 allowing the air flow to decelerate before contacting the heater 14 and lessen the tendency of the air flow to cool the heater 14. Alternatively, the heater 14 can be moved closer to the mouth end insert 8 and farther away from the central air passage 20 to allow the air flow time and/or space sufficient to decelerate to achieve the same cooling-abatement effect.

Preferably, the addition of the frustoconical section 40 provides a larger diameter bore size which can decelerate the air flow so that the air velocity at or about the heater 14 is reduced so as to abate the cooling effect of the air on the heater 14 during puff cycles. Preferably, the diameter of the large (exit) end of the frustoconical section 40 ranges from about 2.0 mm to about 4.0 mm, more preferably about 2.5 mm to about 3.5 mm.

The diameter of the bore of the central air passage 20 and the diameter of the smaller and/or larger end of the frustoconical section 40 can be adjusted to control the resistance to draw of the electronic cigarette 60.

Preferably, the air flow diverter of the various embodiments channels the air flow by controlling the air flow velocity (its speed and/or the direction of the air flow). For example, the air flow diverter can direct air flow in a particular direction and/or control the speed of the air flow. The air flow speed may be controlled by varying the cross sectional area of the air flow route. Air flow through a constricted section increases in speed while air flow through a wider section decreases speed.

In an embodiment, the electronic cigarette 60 is about the same size as a conventional cigarette. In some embodiments, the electronic cigarette 60 can be about 80 mm to about 110 mm long, preferably about 80 mm to about 100 mm long and about 7 mm to about 8 mm in diameter. For example, in an embodiment, the electronic cigarette is about 84 mm long and has a diameter of about 7.8 mm.

In one embodiment, the electronic cigarette 60 of FIGS. 1, 4, 6 and 8 can also include a filter segment upstream of the heater 14 and operable to restrict flow of air through the electronic cigarette 60. The addition of a filter segment can aid in adjusting the resistance to draw.

The outer tube 6 and/or the inner tube 62 may be formed of any suitable material or combination of materials. Examples of suitable materials include metals, alloys, plastics or composite materials containing one or more of those materials, or thermoplastics that are suitable for food or pharmaceutical applications, for example polypropylene, polyetheretherketone (PEEK), ceramic, and polyethylene. Preferably, the material is light and non-brittle.

As shown in FIG. 9, the electronic cigarette 60 can also include a sleeve assembly 87 removably and/or rotatably positioned about the outer tube 6 adjacent the first section 70 of the electronic cigarette 70. Moreover, the sleeve assembly 87 insulates at least a portion of the first section 70 so as to maintain the temperature of the aerosol prior to delivery to the smoker. In an embodiment, the sleeve assembly 87 is rotatable about the electronic cigarette 60 and includes spaced apart slots 88 arranged transversely about the sleeve assembly such that the slots 88 line up with the air inlets 44 in the first section 70 to allow air to pass into the electronic cigarette 60 when a smoker draws a puff. Before or during smoking, the smoker can rotate the sleeve assembly 87 such that the air inlets 44 are at least partially blocked by the sleeve assembly 87 so as to adjust the resistance to draw and/or ventilation of the electronic cigarette 60.

Preferably, the sleeve assembly 87 is made of silicone or other pliable material so as to provide a soft mouthfeel to the smoker. However, the sleeve assembly 87 can be formed in one or more pieces and can be formed of a variety of materials including plastics, metals and combinations thereof. In an embodiment, the sleeve assembly 87 is a single piece formed of silicone. The sleeve assembly 87 can be removed and reused with other electronic cigarettes or can be discarded along with the first section 70. The sleeve assembly 87 can be any suitable color and/or can include graphics or other indicia.

As shown in FIG. 10, the electronic cigarette 60 can also include an aroma strip 89 located on an outer surface 91 of at least one of the first section 70 and the second section 72. Alternatively, the aroma strip 89 can be located on a portion of the sleeve assembly 87. Preferably, the aroma strip 89 is located between the battery of the device and the heater such that the aroma strip 89 is adjacent a smoker's nose during smoking. The aroma strip 89 can include a flavor aroma gel, film or solution including a fragrance material that is released before and/or during smoking. In one embodiment, the flavor aroma of the gel, fluid and/or solution can be released by the action of a puff which may open a vent over the aroma strip when positioned inside the first section 70 (not shown). Alternatively, heat generated by the heater 14 can cause the release of the aroma.

In one embodiment, the aroma strip 89 can include tobacco flavor extracts. Such an extract can be obtained by grinding tobacco material to small pieces and extracting with an organic solvent for a few hours by shaking the mixture. The extract can then be filtered, dried (for example with sodium sulfate) and concentrated at controlled temperature and pressure. Alternatively, the extracts can be obtained using techniques known in the field of flavor chemistry, such as the Solvent Assisted Flavor Extraction (SAFE) distillation technique (Engel et al. 1999), which allows separation of the volatile fraction from the non-volatile fraction. Additionally, pH fractionation and chromatographic methods can be used for further separation and/or isolation of specific compounds. The intensity of the extract can be adjusted by diluting with an organic solvent or water.

The aroma strip 89 can be a polymeric or paper strip to which the extract can be applied, for example, using a paintbrush or by impregnation. Alternatively, the extract can be encapsulated in a paper ring and/or strip and released manually by the smoker, for example by squeezing during smoking the aroma strip 89.

As shown in FIGS. 11 and 12, in an alternative embodiment, the electronic cigarette of FIGS. 1, 4, 6 and 8 can includes a mouth end insert 8 having a stationary piece 27 and a rotatable piece 25. Outlets 24, 24' are located in each of the stationary piece 27 and the rotatable piece 25. One or more of the outlets 24, 24' align as shown to allow aerosol to enter a smoker's mouth. However, the rotatable piece 25 can be rotated within the mouth end insert 8 so as to at least partially block one or more of the outlets 24 in the stationary mouth end insert 27. Thus, the consumer can adjust the amount of aerosol drawn with each puff. The outlets 24, 24' can be formed in the mouth end insert 8 such that the outlets 24, 24' diverge to provide a fuller mouth feel during inhalation of the aerosol.

In another embodiment, the air flow diverter comprises the addition of a second wick element adjacent to but just upstream of the heater 14. The second wick element diverts portions of the air flow about the heater 14.

In another embodiment, as shown in FIG. 15, the electronic cigarette 60 comprises a replaceable cartridge (or first section) 70 and a reusable fixture (or second section) 72, which are coupled together at a threaded connection 205 or by other convenience such as a snug-fit, detent, clamp and/or clasp. The second section 72 can be constructed in accordance with the teachings above regarding the other embodiments such as that shown and described with respect to FIG. 1.

Still referring to FIG. 15, in this embodiment, the first section 70 includes an outer tube 6 (or casing) extending in a longitudinal direction and a liquid supply reservoir in the form of a truncated cylindrical tank reservoir 22 at a location between the connection 205 and a mouthpiece insert 8. Preferably, the tank reservoir 22 comprises a separately formed, self-supporting (discrete) hollow body constructed of a heat-resistant plastic or woven fiberglass. In an embodiment, the tank reservoir 22 can be generally in the form of elongate partial cylinder, one side of which is truncated. In an embodiment, the tank reservoir 22 has a transverse dimension, such as in the direction of arrow "x" in FIG. 16, and is truncated such that the aforementioned transverse dimension is approximately two-thirds of the diameter of the tank reservoir 22. The aforementioned transverse dimension may vary in other embodiments, depending on design requirements such as a desired capacity of the tank or a need for space within the casing 6 for heaters and for channeling airflow. For example, in the embodiment shown in FIG. 15, the tank reservoir 22 has a semi-circular cross-section or a transverse dimension equal to one-half the tank diameter.

In one embodiment, the reservoir tank 22 can be a construction separate of the casing 6 and comprises a longitudinally extending planar panel 101 and an arcuate, longitudinally extending panel 103. The arcuate panel 103 preferably conforms or mates with an interior surface 127 of the outer tube 6. It is envisioned that the tank reservoir 22 may be held in place against the interior 127 of the outer casing 6 by conveniences such as spaced ridges 333 and 333' at predetermined locations along the interior 127 of the outer casing 6 or a rail/slide connection (e.g., see FIG. 22), a friction fit or a snap fit or other convenience. In addition or in lieu thereof, discs of liquid absorbent material 10 and 15 may be positioned against interior portions of the reservoir tank 22 to retain the reservoir tank 22 in place and also to absorb any liquid that might escape inadvertently from the tank reservoir 22 or the wick 28. The discs 10, 15 would be each provided apertures 11 to allow air and/or aerosol to pass therethrough.

In the preferred embodiment, a wick 28 is in communication with the interior of the supply reservoir 22 and in communication with a heater 14 such that the wick 28 draws liquid via capillary action from the reservoir tank 22 into proximity of the heater 14. The wick 28 is preferably a bundle of flexible filaments whose end portions 29 and 31 are disposed within the confines of the tank reservoir 22. Preferably, the contents of the liquid supply reservoir is a liquid as previously described together with the end portions 29, 31 of the wick 28. Preferably the end portions 29, 31 of the wick 28 occupy substantial portions of the tank interior such that orientation of the smoking article 60 does not impact the ability of the wick 28 to draw liquid. Optionally, the reservoir tank 22 may include filaments or gauze or a fibrous web to maintain distribution of liquid within the tank reservoir 22.

Preferably, the heater 14 may comprise a coil winding of electrically resistive wire about a portion of the wick 28. Instead or in addition, the heater may comprise a single wire, a cage of wires, printed "wire", metallic mesh, or other arrangement instead of a coil. The heater 14 and the associated wick portion 28 may be disposed centrally of the planar panel 101 of the tank reservoir 22 as shown in FIG. 16, or could be placed at one end portion thereof or may be one or two or more heaters 14 disposed either centrally or at opposite end portions of the planar panel 101.

Referring now to FIGS. 15 and 16, in an embodiment, a flow diverter 100 is provided adjacent the heater 14. The diverter 100 may take the form of a generally oval shield or wall 105 extending outwardly from the plane of the planar panel 101 and proximate to the heater 14 and the wick 28 such that an approaching air stream is diverted away from the heater 14 so that the amount of air drawn directly across the heater is reduced in comparison the arrangements lacking a flow diverter 100.

Preferably, the oval wall 105 is open ended so that when the heater 14 is activated to freshly produce aerosol in its proximity, such supersaturated aerosol may be withdrawn from the confines of the diverter 100. Not wishing to be bound by theory, such arrangement releases aerosol by utilizing the drawing action or venturi effect of the air passing by the heater 14 and the open ended diverter 100. Optionally, holes 107 are provided in the wall 105 of the diverter 100 so that the drawing action of the air tending to withdraw aerosol from the confines of the diverter 100 does not work against a vacuum. These holes 107 may be sized to provide an optimal amount of air to be drawn into the confines of the diverter 100. Thereby, the amount of air being drawn into contact with the heater 14 is reduced and controlled, and a substantial portion of the approaching air stream is diverted and by-passes the heater 14, even during aggravated draws upon the electronic cigarette 60.

In addition, the holes 107 may be utilized for routing of end portions 27, 27' of the heater 14 or separate holes or notches may be provided. In the embodiment of FIG. 16, the end portions 27, 27' of the heater 14 and the electric leads 26 and 26' are connected at electric contacts 111, 111' established on the planar panel 101 adjacent the location of the diverter 100. The electrical contacts 111, 111' may instead be established on the wall 105' itself, as shown in FIG. 17.

Referring back to FIG. 16, the oval diverter shield 105 is symmetrical along the longitudinal axis such that the diverter 100 may be placed in the orientation as shown in FIG. 16 or 180° from that orientation, which facilitates manufacture and assembly of the smoking article 60.

Referring now to the FIG. 17, the diverter 100 may be configured instead to have an oval wall 105' that includes an open-ended downstream portion 109, which further facilitates the release of aerosol from about the heater 14. It is envisioned that the wall 105 of the diverter 100 may take a form of a shallow "u" or "v" and may include an arched portion at least partially superposing the heater 14. In the embodiments shown in FIGS. 15, 16 and 17, the oval shield wall 105 is oriented with its longitudinal axis generally parallel to the longitudinal axis of the smoking article 60.

In FIGS. 18, 19 and 20 the orientation of the diverter 100 and the heater 14 may instead be transverse to the longitudinal axis of the smoking article 60. Whereas one of the former orientations may minimize disturbance of airflow, the other orientation may produce a greater number of eddies or the like to promote mixing of air with aerosol.

With regard to the various embodiments shown in FIGS. 15-20, it is envisioned that tank reservoir 22 may have a cap 335 at one end thereof. With the cap 335 removed, the tank reservoir 22 may be filled with liquid prior to closure with the cap 335. A friction fit or snap close arrangement may be used to keep the cap 335 in place or the cap 335 may be heat-fused into place. It is envisioned that other portions of the tank reservoir 22 structure may be used for filling. For example, the planar panel 101 may be made as a separate, attachable piece for filling operations instead of cap 335. A separate, attachable planar panel 101 is advantageous in that the diverter structure 100 may be attached to or integrally formed with the planar panel 101, before attaching the panel 101 to the remainder of the tank reservoir 22. Such arrangement also facilitates installation of the wick 28 and heater 14 within the confines of the diverter 100. It is also envisioned that the diverter 100 might be a separate piece in the form of a tub or shoe with a bottom wall having apertures for receiving end portions 29, 31 of the wick 28. Such arrangement would facilitate installation of the wick 28 and the heater 14 within the confines of separate diverter 100 for subsequent attachment to the planar wall 101.

Still referring now to FIGS. 15-20, when a smoker draws upon the mouthpiece portion of the electronic smoking article 60, the pressure sensor and control circuitry 16 activate the heater 14 in accordance with a power cycle such as ones previously described. Air enters the smoking article in these embodiments through the one or more ports 44, 44' and then is drawn toward the mouthpiece 8 via the channel 110 defined between the reservoir tank 22 and opposing interior surfaces 127 of the outer casing 6. Thereafter, the aerosol produced by the heater 14 and the wick 28 is mixed with the air and the resultant aerosol (vapor) is drawn through the multi-ported mouthpiece 8.

With the inclusion of the diverter 100 in these embodiments, a substantial portion of the airstream entering the channel 110 bypasses the heater 14 such that a heavy drawing action on the smoking article 60 does not increase or impose a counteractive cooling effect upon the heater 14, which as previously described, may inhibit desired heater operation. Instead, the heater 14, being shielded by the diverter 100, can generate an aerosol with only a controlled or reduced amount of cooling effect from a passing air stream.

Figure 21:
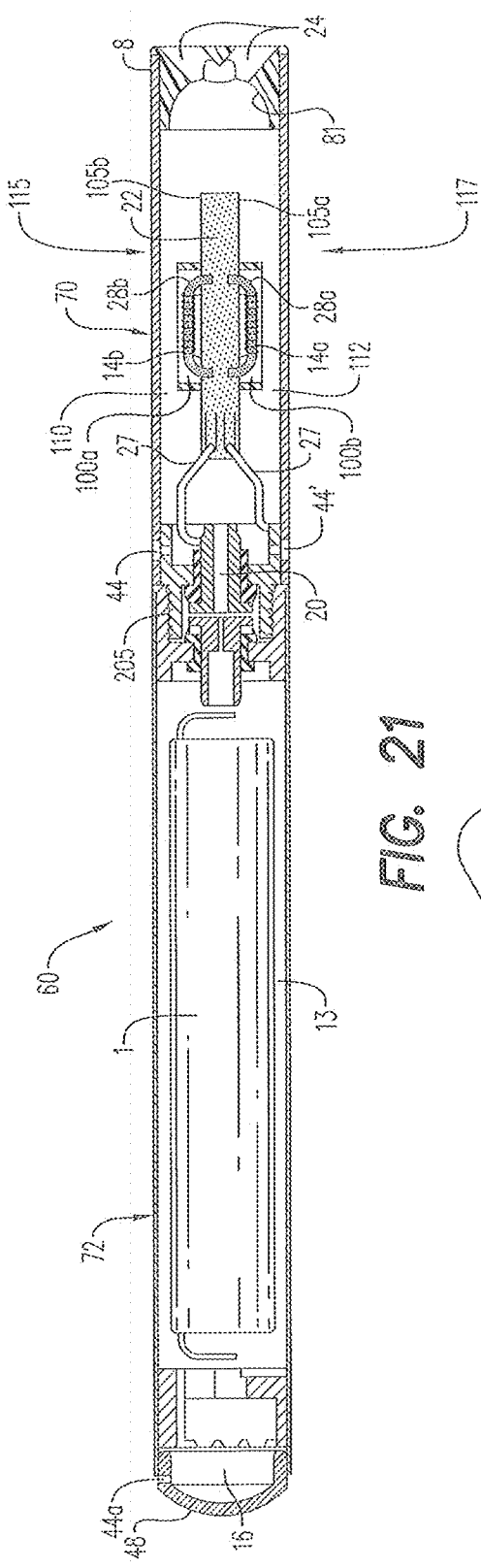
FIG. 21 is a cross-sectional view of an embodiment wherein an electronic cigarette includes a tank reservoir, two heaters and two air flow diverters.
Figure 22:
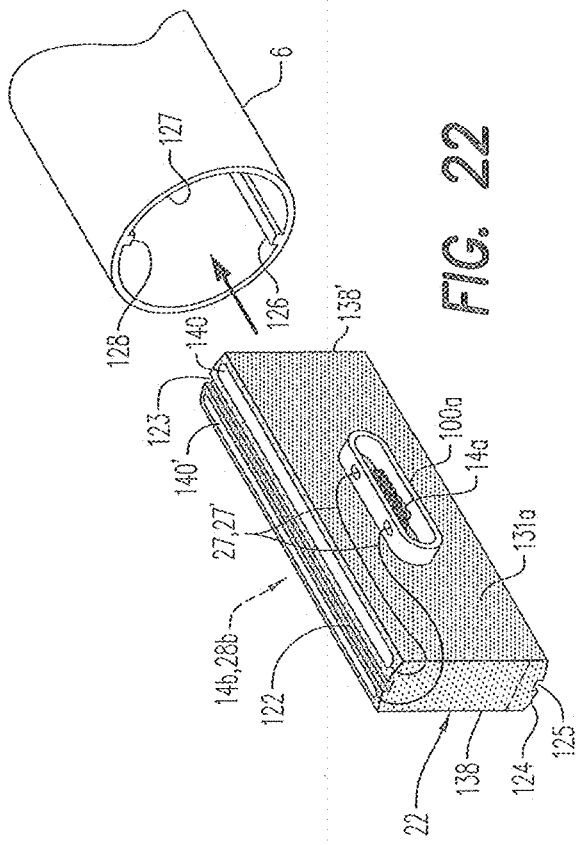
FIG. 22 is an enlarged perspective view of the tank reservoir, the two air flow diverters and heaters of the electronic cigarette of FIG. 21.

Referring now to FIGS. 21 and 22, in another embodiment, the reservoir tank 22 is in the form of a hollow, generally rectangular body which is insertable into the confines of the outer casing 6. In an embodiment, the top panel 122 and the bottom panel 124 can be contoured to match the curvature of the interior surfaces of the inner surface 127 of the outer tube 6 so as to provide a friction fit between the reservoir tank 22 and the outer casing 6. In another embodiment, the top panel 122 and the bottom panel 124 can each include a groove 123, 125 extending longitudinally along the length of the tank reservoir 22. In this embodiment, the grooves 123, 125 mate with rails 126, 128 extending longitudinally along the inner surface 127 of the outer casing 6 so that the reservoir tank 22 can be slid and guided into position relative to the mouthpiece insert 8. In both embodiments, the tank reservoir 22 is preferably spaced away from the mouthpiece 8 by a predetermined distance so as to provide space and opportunity for mixing of the aerosol generated at the heaters 14a, 14b and the airflow passing thereby. Optionally, either or both of the rails 126, 128 and the grooves 123 and 125 may be provided with detents, catches or other arrangement to lock the reservoir tank 22 into a predetermined location along the outer casing 6. The ridges 333, 333' shown in FIG. 15 may be used instead or in addition for the placement and retention of the tank reservoir 22 of FIG. 21.

In an embodiment, a heater 14a and a wick 28a is located at a preferably central location along one side panel or panel 131a, which is provided with a diverter 100a in accordance with the teachings above with reference to FIGS. 15-20. Although the orientation of the heater 14a, wick 28a and diverter 100a are shown to be in the longitudinal orientation, they instead could be oriented in a transverse direction and more than one of such arrangement could be disposed along the side panel 131a. Preferably, a similar arrangement is provided on the opposite side panel 131b such that the reservoir tank 22 feeds two wicks 28a, 28b or more. Although the heaters 14a and 14b are shown in an opposing relation, they may be offset from one-another or be located on the same side panel 131a, 131b. With reference also to FIG. 27, it is also envisioned that the tank reservoir 22 could be compartmentalized or partitioned such that first and second liquids are retained separately within discrete compartments 22' and 22" within the tank reservoir 22. In such case, the first heater 14' and wick 28' can be operative with a first compartment to aerosolize the first liquid; and the second heater 14" and wick 28" can be operative with a second compartment to aerosolize the second liquid. It is envisioned the control circuitry 16 may be programmed to operate the heaters 14', 14" separately, each according to parameters tailored to the requirements for aerosolizing the two (or more) separate liquid components.

Figure 23:
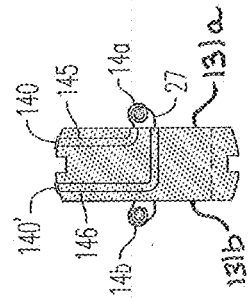
FIG. 23 is a cross-sectional representation of an embodiment wherein electrical connections to the heaters are internal of the tank reservoir.

Referring now to FIGS. 21-23, electrical connection to the heaters 14a and 14b may include provision of electrical contact 140, 140' atop the tank reservoir 22, each preferably in the form of a longitudinal stripe or track extending along the a length of the top panel 122. In lieu or in addition the contacts 140, 140' may be located along the end panels 138 and/or 138' of the tank reservoir 22. Electrical connection from the anode and cathode of the battery 1 is effected through leads 26 that can either be biased into contact with the contact stripes 140, 140' or be electrically connected as part of assembly of the electronic smoking article 60. Connections to heaters 14a, 14b may be established externally of the tank reservoir 22 by routing end portions 27, 27' of the heater 14, 14' through notches or holes provided in the diverter wall 105 or other convenience, such as shown in FIG. 22.

Referring now in particular to FIG. 23, alternatively, the end portions 27, 27' of each heater 14a, 14b may be connected to the same or their own the contact stripes 140, 140' via electrical leads 145, 146 disposed internally of the tank reservoir 22.

Still referring to FIG. 22, the bottom panel 124 may be a separately formed piece which snap fits or is heat sealable with the rest of the reservoir tank structure so as to facilitate assembly and to facilitate establishing electrical connections and for the filling of the tank reservoir 22. It is also envisioned that other portions of the tank 22 may be selected as the panel to serve as a separate piece. Likewise, the diverters 100a, 100b may be formed integrally with the side panels 131a or 131b or formed as a separate piece such as in the form of a tub or shoe.

As with the other embodiments, as air is drawn into the smoking article 60 via air inlets 44, 44' and then along the side panels 131a and 131b the of the tank reservoir 22. A substantial portion of air is diverted and cause to bypass the immediate area of the heater and wick assemblies by the presence and proximity of the flow diverters 100. Aerosol formed in regions proximal of the heaters 14a and 14b are drawn and mixed with the airflow before being drawn through the multi-ported mouthpiece insert 8.

Referring now to FIGS. 24 and 25, in another embodiment, there is provided a tank reservoir 22 such as in the embodiments described with reference to FIGS. 21-23. However in this embodiment, a wick 28 has an end portion 29 which extends along the interior of the tank reservoir 22 and end portion 31 which extends in a longitudinal direction outwardly from an end panel 138 of the tank reservoir 22. The outwardly extending portion 31 of the wick 28 cooperates with a heater 14 as previously described. Optionally a cap 139 is provided at the free end of the wick 28. The end portions 27, 27' of the heater 14 may be connected with the contact stripes 140, 140' or other arrangements as previously described, including a direct connection with the leads 26 of the smoking article 60.

In this embodiment, preferably a flow diverter 100c is disposed about both the wick portion 31 and the heater 14 and takes the form of a cylinder, which has an open downstream end portion. In operation, air is drawn along the tank reservoir 22 as aerosol is generated within the confines of the flow diverter 100c. As the air is drawn past the flow diverter 100c, freshly produced aerosol is drawn from the confines of the flow diverter 100c and mixed with the air stream prior to being drawn through the mouthpiece insert 8.

In an embodiment, the flow diverter 100c is provided with ports or holes 146 so as to allow some air to enter the confines of the flow diverter of 100c so that withdrawal of freshly produced aerosol is facilitated. By such arrangement, the aerosol is withdrawn without having to work against a vacuum.

In another embodiment the end cap 139 may include radial extensions 139' to promote mixing of freshly produced aerosol with the passing airstream. It is envisioned that the radial extension 139' may be disc-like to provide collision sites to break apart and/or collect larger particles in the aerosol.

Whereas the embodiment shown in FIGS. 24 and 25 show a single diverter 100c at a downstream end of the tank reservoir 22, another similar wick/heater/diverter arrangement may be constructed at the upstream end of the tank reservoir 22 in addition to the one shown in FIG. 25 (or in lieu thereof).

Referring now to FIG. 26, a rectangular form of tank reservoir 22 such as described with reference to FIGS. 21-23 may be partitioned by an internal panel 147 so that the upstream wick 28' draws one liquid from one compartment 22', and the downstream wick 28' draws from a second compartment 22". Such arrangement might include provision for separate connection of the heaters so that an upstream heater 14' might heat according to different operating parameters from a downstream heater 14 to accommodate different heating requirements for formulations or components thereof.

Although the tank reservoir 22 of FIGS. 24-26 is shown and described as rectangular, the tank reservoir 22 can instead have other shapes, such as cylindrical body that is undersized with respect to the interior of the outer casing 6 so as to permit airflow to pass thereby.

The above teachings provide examples of an electronic smoking article 60 being modified to include the air flow diverter, all which change the speed and/or direction of the airstream to counteract the tendency of the airstream to cool the heater 14.

The teachings herein are applicable to electronic cigars, and references to "electronic cigarette(s)" is intended to be inclusive of electronic cigars and the like. Moreover, references to "electronic smoking articles" is intended to be inclusive of electronic cigars, electronic cigarettes and the like.

When the word "about" is used in this specification in connection with a numerical value, it is intended that the associated numerical value include a tolerance of ±10% around the stated numerical value. Moreover, when reference is made to percentages in this specification, it is intended that those percentages are based on weight, i.e., weight percentages.

Moreover, when the words "generally" and "substantially" are used in connection with geometric shapes, it is intended that precision of the geometric shape is not required but that latitude for the shape is within the scope of the disclosure. When used with geometric terms, the words "generally" and "substantially" are intended to encompass not only features which meet the strict definitions but also features which fairly approximate the strict definitions.

It will now be apparent that a new, improved, and nonobvious electronic cigarette has been described in this specification with sufficient particularity as to be understood by one of ordinary skill in the art. Moreover, it will be apparent to those skilled in the art that modifications, variations, substitutions, and equivalents exist for features of the electronic cigarette which do not materially depart from the spirit and scope of the invention. Accordingly, it is expressly intended that all such modifications, variations, substitutions, and equivalents which fall within the spirit and scope of the invention as defined by the appended claims shall be embraced by the appended claims.

We claim:

1. An electronic vaping device comprising:

a tank reservoir configured to contain a liquid material, the tank reservoir defining at least one opening therein;

a mouth-end insert including, at least one outlet;

a wick including a first portion, a second portion, and an end portion, the first portion and the end portion extending through the at least one opening of the tank reservoir;

a heater at least partially in contact with the second portion of the wick;

an airflow diverter adjacent the end portion of the wick, the airflow diverter including a cylindrical wall extending around the second portion of the wick, the cylindrical wall configured to divert air away from the heater; and a power supply configured to supply power to the heater.

2. The electronic vaping device of claim 1, wherein at least a portion of the wick extends in a longitudinal direction within the electronic vaping device.

3. The electronic vaping device of claim 1, wherein the cylindrical wall has a first end and a second end.

4. The electronic vaping device of claim 3, wherein the first end of the cylindrical wall is adjacent the tank reservoir.

5. The electronic vaping device of claim 4, wherein the cylindrical wall defines at least one hole therein.

6. The electronic vaping device of claim 5, wherein the at least one hole is at the first end of the cylindrical wall.

7. The electronic vaping device of claim 1, wherein the power supply includes a battery.

8. The electronic vaping device of claim 1, wherein the heater is a wire coil.

9. The electronic vaping device of claim 1, wherein the heater includes stainless steel, copper, a copper alloy, a nickel-chromium alloy, an iron aluminum alloy, an iron chromium alloy, a super alloy, an iron aluminide, a nickel aluminide, or any combination thereof.

10. The electronic vaping device of claim 1, wherein the mouth-end insert includes at least two outlets.

11. The electronic vaping device of claim 10, wherein the at least two outlets are diverging outlets, the diverging outlets angled at about 5° to about 60° in relation to a longitudinal direction of the electronic vaping device.

12. A cartridge of an electronic vaping device, the cartridge comprising:

a tank reservoir configured to contain a liquid material, the tank reservoir defining at least one opening therein;

a mouth-end insert including,
at least one outlet;

a wick including a first portion, a second portion, and an end portion, the first portion and the end portion extending through the at least one opening of the tank reservoir;

a heater at least partially in contact with the second portion of the wick; and an airflow diverter adjacent the end portion of the wick, the airflow diverter including a cylindrical wall extending around at least the second portion of the wick, the cylindrical wall configured to divert air away from the heater.

13. The cartridge of claim 12, wherein at least a portion of the wick extends in a longitudinal direction within the electronic vaping device.

14. The cartridge of claim 12, wherein the cylindrical wall has a first end and a second end.

15. The cartridge of claim 14, wherein the first end of the cylindrical wall is adjacent the tank reservoir.

16. The cartridge of claim 15, wherein the cylindrical wall defines at least one hole therein.

17. The cartridge of claim 16, wherein the at least one hole is at the first end of the cylindrical wall.

18. The cartridge of claim 12, further comprising:
a cap covering the end portion of the wick.

* * * * *